US010342244B2

(12) United States Patent
Barrett-Reis et al.

(10) Patent No.: US 10,342,244 B2
(45) Date of Patent: *Jul. 9, 2019

(54) INFANT FORMULAS CONTAINING DOCOSAHEXAENOIC ACID AND LUTEIN

(71) Applicant: ABBOTT LABORATORIES, Abbott Park, IL (US)

(72) Inventors: Bridget Barrett-Reis, Dublin, OH (US); Pamela T. Price, Granville, OH (US); Amy Mackey, Columbus, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/829,142

(22) Filed: Dec. 1, 2017

(65) Prior Publication Data
US 2018/0077952 A1 Mar. 22, 2018

Related U.S. Application Data

(63) Continuation of application No. 14/512,144, filed on Oct. 10, 2014, now Pat. No. 9,861,120, which is a
(Continued)

(51) Int. Cl.
*A23L 2/66* (2006.01)
*G01N 33/82* (2006.01)
(Continued)

(52) U.S. Cl.
CPC ................. *A23L 2/66* (2013.01); *A23L 33/10* (2016.08); *A23L 33/115* (2016.08); *A23L 33/17* (2016.08);
(Continued)

(58) Field of Classification Search
CPC ............ A61K 2300/00; A23V 2002/00; A23V 2250/211; A23V 2250/1868;
(Continued)

(56) References Cited

U.S. PATENT DOCUMENTS 5,234,702 A 8/1993 Katz
5,382,714 A 1/1995 Khachik
(Continued)

FOREIGN PATENT DOCUMENTS

AU 199647091 9/1996
AU 2003251396 12/2003
(Continued)

OTHER PUBLICATIONS

Canfield, Louise M., et al. Multinational study of major breast milk carotenoids of healthy mothers, Eur J Nutr 42: 133-141, 2003 (Year: 2003).*
(Continued)

*Primary Examiner* — Hong T Yoo
(74) *Attorney, Agent, or Firm* — Calfee, Halter & Griswold LLP

(57) ABSTRACT

Disclosed are infant formulas and corresponding methods of using them to promote retinal health and vision development in infants. The formulas, which are free of egg phospholipids and comprise fat, protein, carbohydrate, vitamins, and minerals, including docosahexaenoic acid and, on a ready-to-feed basis, at least about 50 mcg/liter of lutein, wherein the weight ratio of lutein (mcg) to docosahexaenoic acid (mg) is from about 1:2 to about 10:1. The formulas are also believed to be especially useful in reducing the risk of retinopathy of prematurity in preterm infants.

16 Claims, 2 Drawing Sheets

Related U.S. Application Data continuation of application No. 11/646,671, filed on Dec. 28, 2006, now abandoned, which is a continuation-in-part of application No. 11/584,704, filed on Oct. 20, 2006, now Pat. No. 7,829,126.

(60) Provisional application No. 60/730,283, filed on Oct. 26, 2005.

(51) Int. Cl.
*A23L 33/00* (2016.01)
*A23L 33/10* (2016.01)
*A23L 33/115* (2016.01)
*A23L 33/17* (2016.01)

(52) U.S. Cl.
CPC .............. *A23L 33/40* (2016.08); *G01N 33/82* (2013.01); *A23V 2002/00* (2013.01); *G01N 2800/38* (2013.01)

(58) Field of Classification Search
CPC ........ A23V 2250/1882; A23V 2200/30; A23V 2200/00; A23L 33/40
See application file for complete search history.

(56) References Cited

U.S. PATENT DOCUMENTS

| | | | |
|---|---|---|---|
| 5,550,156 A | 8/1996 | Kyle | |
| 5,648,564 A | 7/1997 | Ausich et al. | |
| 5,955,102 A | 9/1999 | Gorenbein et al. | |
| 6,080,787 A | 6/2000 | Carlson et al. | |
| 6,261,598 B1 | 7/2001 | Runge | |
| 6,262,284 B1 | 7/2001 | Khachik | |
| 6,306,908 B1 | 10/2001 | Carlson et al. | |
| 6,365,218 B1 | 4/2002 | Borschel et al. | |
| 6,455,072 B1 | 9/2002 | Peters | |
| 6,495,599 B2 | 12/2002 | Auestad et al. | |
| 6,509,029 B2 | 1/2003 | Runge | |
| 6,589,576 B2 | 7/2003 | Borschel et al. | |
| 6,649,195 B1 | 11/2003 | Gorsek | |
| 6,727,373 B2 | 4/2004 | Bijl et al. | |
| 6,811,801 B2 | 11/2004 | Nguyen | |
| 7,090,862 B2 | 8/2006 | Barrett-Reis et al. | |
| 7,090,879 B2* | 8/2006 | Albrecht ................... | A23L 2/39 426/262 |
| 7,173,145 B2 | 2/2007 | Khachik | |
| 7,829,126 B2* | 11/2010 | Barrett-Reis .......... | A23L 33/105 426/72 |
| 8,263,147 B2* | 9/2012 | Barrett-Reis .......... | G01N 33/82 426/72 |
| 9,861,120 B2* | 1/2018 | Barrett-Reis .......... | G01N 33/82 |
| 2001/0019724 A1 | 9/2001 | Runge | |
| 2002/0132800 A1 | 9/2002 | Popp | |
| 2003/0104078 A1* | 6/2003 | Barrett-Reis ........ | A61K 31/355 424/727 |
| 2003/0118703 A1 | 6/2003 | Nguyen et al. | |
| 2003/0228392 A1 | 12/2003 | Zimmer | |
| 2005/0002988 A1 | 1/2005 | Mizumoto et al. | |
| 2005/0031736 A1 | 2/2005 | Nguyen et al. | |
| 2005/0106272 A1 | 5/2005 | Lang et al. | |
| 2005/0147731 A1 | 7/2005 | Holub et al. | |
| 2005/0208179 A1 | 9/2005 | Albrecht et al. | |
| 2006/0088574 A1 | 4/2006 | Manning et al. | |
| 2006/0270739 A1 | 11/2006 | Johnson et al. | |
| 2015/0024112 A1 | 1/2015 | Barrett-Reis | |

FOREIGN PATENT DOCUMENTS

| | | |
|---|---|---|
| AU | 2006306366 | 5/2007 |
| CA | 2458325 | 3/2003 |
| CA | 2625001 | 5/2007 |
| CN | 1481829 | 3/2004 |
| EP | 0981969 | 8/1999 |
| FR | 2882894 | 9/2006 |
| JP | 20025513411 | 5/2002 |
| JP | 2003026589 | 1/2003 |
| JP | 2005065525 | 3/2005 |
| WO | 1998045241 | 10/1998 |
| WO | 2000078217 | 12/2000 |
| WO | 200178530 | 10/2001 |
| WO | 2002200208 | 3/2002 |
| WO | 2002041711 | 5/2002 |
| WO | 2003022288 | 3/2003 |
| WO | 2005009422 | 2/2005 |
| WO | 2005065669 | 7/2005 |
| WO | 2005068409 | 7/2005 |
| WO | 2005087208 | 9/2005 |
| WO | 2005110375 | 11/2005 |
| WO | 2006116755 | 11/2006 |
| WO | 2007050521 | 5/2007 |

OTHER PUBLICATIONS

Zimmer, J Paul, et al. Possible influences of lutein and zeaxanthin on the developing retina, Clincial Opthalmology 2007:1(1) 25-35 (Year: 2007).*

Gossage, Cynthia, et al. Carotenoid composition of human milk during the first month postpartum and the response to B-carotene supplementation, Am J Clin Nutr 2002: 76: 193-7 (Year: 2002).*

Bettler, Jodi, et al. Serum lutein concentrations in healthy term infants fed human milk or infant formula with lutein, Eur J Nutr (2010) 49:45-51 (Year: 2010).*

Jewell, et al., "Nutritional factors and visual functions in premature infants," Proceedings of the Nutrition Society, 2001, 171-178.

Jorgensen et al., "Is There a Relation between Docosahexaenoic Acid Concentration in Mother's Milk and Visual Development in Term Infants?" J. of Pediatric Gastroenterology & Nutrition vol. 32(3) pp. 293-296 (Mar. 2001).

Khachik et al., "Bioavailability, Metabolism, and Possible Mechanism of Chemoprevention by Lutein and Lycopene in Humans," in Food Factors for Cancer Prevention, Ohigashi et al., editors, Springer-Verlag (Tokyo), pp. 542-547 (1997).

Khachik et al., "Identification of lutein and zeaxanthin oxidation products in human and monkey retinas," Invest. Ophthalmol. Vis. Sci., 38: 1802-1811 (1997).

Khachik et al., "Identification, Quantification, and Relative Concentrations of Carotenoids and Their Metabolites in Human Milk and Serum," Analytical Chemistry, vol. 69, No. 10, May 16, 1997.

Khachik et al., "Lutein, Lycopene and Their Oxidative Metabolism in Chemoprevention of Cancer", J. Cellular Biochemistry, Supplement 22: 236-246 (1995).

Khachik et al., "Separation and identification of carotenoids and their oxidation products in extracts of human plasma," Anal. Chem., 64(18): 2111-2122 (1992).

Khachik, et al., "Transformations of selected carotenoids in plasma, liver, and ocular tissues of humans and in non-primate animal models," J. Invest. Ophthalmol. Vis. Sci., 43: 3383-3392 (2002).

Koh, et al., "Plasma and macular responses to lutein supplements in subjects with and without age related maculopathy: a pilot study", Experimental Eye Research, vol. 79 (2004), pp. 21-27.

Koletzko, et al., "Global Standard for the Composition of Infant Formula: Recommendations of an ESPGHAN Coordinated International Expert Group," J. Ped Gastroenterology and Nutrition (Nov. 2005) 41(5):584-599.

Lonnerdal, Bo. "Dietary Factors Affecting Trace Element Bioavailability from Human Milk, Cow's Milk, and Infant Formulas," Progress in Food and Nutrition Science (1985), vol. 9, pp. 35-62.

Macias, Conseulo "Changes in the Concentration of Carotenoids, Vitamin A, Alpha-Tocopherol and Total Lipids in Human Milk Throught Early Lactation," Annals of Nutrition & Metabolism, 45, pp. 82-85, 2001.

Mactier, et al. "Vitamin A and preterm infants: what we know, what we don't know, and what we need to know," Arch Dis Child Fetal Neonatal Ed. 2005; 90:F103-108.

(56) References Cited

OTHER PUBLICATIONS

Makrides et al., "A critical appraisal of the role of dietary long chain polyunsaturated fatty acids on neural indices of term infants: A randomised, controlled trial," Pediatr. (2000) 105:32-38.
Makrides, et al., "Effect of maternal docosahexaeonic acid (DHA) supplementation on breast milk composition," Eur. J. Clin Nutr., (1996), 50: 352-357.
Makrides et al., "Fatty acid composition of brain, retina, and erythrocytes in breast- and formula-fed infants," Am. J. Cli. Nutr. (1994) 60:189-194.
Miller et al. "Calculating Standard Drink Units: International Comparisons," British Journal of Addiction (1991), vol. 86, pp. 43-47.
Naguib, Yousry, "Carotenoids Come of Age," Functional Foods & Nutraceuticals, pp. 58-70 (Mar. 2003).
Naguib, Yousry, M.A. "Antioxidant Activities of Astaxanthin and Related Carotenoids," Agric. Food Chem. 48, pp. 1150-1154, 2000.
National Academy of Sciences, Infant Formula—Evaluating the Safety of New Ingredients (2004), Ch. 3—Comparing Infant Formulas with Human Milk, pp. 41-54.
Neuringer et al., "Visual Development: Neural basis and new assessment methods," Journal of Pediatrics, vol. 143(4), pp. S87-S95 (2003).
Neuringer, Martha. "Infant Vision and Retinal Function in Studies of Dietary Long-Chain Polyunsaturated Fatty Acids: Methods, Results, and Implications," Am J Clin Nutr (2000), 71(suppl), 256S-267S.
Nguyen, Minhthy et al. "Lycopene, Natural Food Colorants: Science and Technology," Ohio State University 2000.
Olmedila, et al., "Lutein in Patients with Cataracts and Age-Related Macular Degeneration: A Long-Term Supplementation Study,"Journal of the Science of Food and Agriculture, 2001.
O'Neil, et al., "Chromatographic Analysis of CIS/Trans Carotenoid Isomers,"Journal of Chromatography, 624, pp. 235-252, 1992.
Rapp, et al., "Lutein and zeaxanthin concentrations on rod outer segment membranes from perifoveal and peripheral human retina", Investigative Opthamology & Visual Science, vol. 41(5), pp. 1200-1209 (Apr. 2000).
Roche Pharmaceuticals, Vitamins and Fine Chemicals for use in Pharmaceuticals, Apr. 2003.
Roche Vitamins Ltd, Roche Launches New Lutein Product Forms, Apr. 16, 2003, accessed at www.newhope.com/print/19110.
S-26 HA: Allergies run in families—Wyeth's S26 HA infant formula (prior to 2005).
Seddon, et al., "Dietary Carotenoids, Vitamins A, C, and E, and Advanced Age-Related Macular Degeneration," JAMA, Nov. 9, 1994, vol. 272(18), pp. 1413-1420 [cited in Oct. 10, 2012.
Smidt, Carsten, Effect of LifePak Supplementation on Antioxidant Status Using Photonic Raman Spectroscopy, Pharmanex LLC 2003.
Snodderly, et al. "Evidence for protection against age-related macular degeneration by carotenoids and antioxidant vitamins," Am. J. of Clinical Nutrition, (1995) 62(Suppl.), 1448S-61S.
Snodderly, et al., "The Influence of Supplemental Lutein and Docosahexaenoic Acid on Their Serum Levels and on Macular Pigment", Invest. Opthamol. Vis. Sci. 46(5), E-abstract, 1766 (2005).
Sommerburg, et al., "Carotenoid Supply in Breast-Fed and Formula-Fed Neonates," Eur. J. Pediatr., 159, pp. 86-90, 2000.
Szabo, George S.A. "The Problem and Solution Approach in the European Patent Office," Int. Rev. Indust. Property & Copyright (1995), vol. 26, pp. 457-487.
Terao, J., "Antioxidant Activity of β-Carotene-Related Carotenoids in Solution" LIPIDS, vol. 24, No. 7, 1989.
Thomson et al., "Elevated Retinal Zeaxanthin and Prevention of Light-Induced Photoreceptor Cell Death in Quail," Invest. Ophthalmol. Vis. Sci. (2002), vol. 43, pp. 3538-3549.
Thurnham, David, Carotenoids: Functions and Fallacies Proceedings of the Nutrition Society, 53, pp. 77-87, 1994.
Westmead Children's Hospital Feeding Guide (Fifth Edition 2005).
"What are Natural Cartienoids? And how can your Child Against Infection? Natural Carotenoids and Protection Against it," Wyeth, The Pediatric Nutrition Network, http://www.wyethnutrition.com.my/nutritionfull.asp?ID=3, May 4, 2003.
Research and Development, Wyeth, http://www.wyethnutritionals.com/about/research.html, Aug. 13, 2002.
Decision Rejecting Opposition in EP1945045B1 dated Jan. 10, 2018.
Statement of Grounds of Appeal by Nestec SA in EP1945045 dated May 21, 2018.
Reply to Appeal by Abbott Laboratories in EP1945045 dated Oct. 4, 2018.
Declaration and C.V. of Seamus McSweeney filed in Appeal of EP1945045 dated May 2018.
Declaration and C.V. of Dr Jose Saavedra filed in Appeal of EP1945045 dated May 2018.
Lucas, et al. "Creamatocrit: simple clinical technique for estimating fat concentration and energy value of human milk," British Medical Journal (1978), vol. 1, pp. 1018-1020.
Records from Wyeth Nutrition for composition of S-26 infant formula from Dec. 2002 to Feb. 2004 filed in Appeal of EP1945045.
King, Suzy "Egg Allergy" 2002.
Search Report for EP Application No. 10189228.9 dated Jan. 5, 2011.
Communication pursuant to Article 94(3) for EP Application No. 10189228.9 dated Mar. 30, 2012.
Communication pursuant to Article 94(3) for EP Application No. 10189228.9 dated Mar. 25, 2015.
Further Exam Report in ID Application No. WO 0200901289 dated Jul. 26, 2013.
Office Action in IL Application No. 217636 dated Aug. 29, 2016.
Office Action in IL Application No. 217636 dated Jan. 15, 2017.
Office Action issued in JP Application No. 2008-537844 dated May 10, 2011.
Final Rejection from JP Application No. 2008-537844 dated Oct. 4, 2011.
Office Action for JP Application No. 2012-028860 dated Oct. 1, 2013.
Notice of Allowance for JP Application No. 2012-028860 dated Jun. 16, 2014.
Preliminary Rejection of KR Application No. 10-2008-7010061 dated Jul. 11, 2011.
Preliminary Rejection of KR Application No. 10-2011-7021428 dated Nov. 9, 2012.
Office Action from MY Application No. PI 2011004051 dated Jul. 31, 2013.
Office Action from MX Application No. MX/a/2008/005338 dated Dec. 10, 2011.
Office Action from MX Application No. MX/a/2012/003044 dated Sep. 13, 2016.
Office Action from PH Application 1-2008-500899 dated Jul. 10, 2013.
Office Action from PH Application 1-2008-500899 dated Sep. 17, 2013.
Notice of Allowance for PH Application 1-2008-500899 dated Dec. 20, 2013.
Office Action from VN Application No. 1-2012-02128 dated Sep. 18, 2012.
Office Action from VN Application No. 1-2012-02128 dated Oct. 1, 2018.
Office Action for RU Application No. 2008120696 dated Apr. 19, 2011.
Written Opinion issued from SG Application No. 200802192-5 dated May 7, 2009.
Examiner's Report from AU Application No. 2011218634 dated Oct. 10, 2012.
Office Action from IL Application No. 190479 dated Feb. 21, 2011.
Exam Report from in Application No. 993/MUMNP/2008 dated Jun. 24, 2010.
U.S. Appl. No. 10/012,383, filed Dec. 12, 2001—Nguyen, "Methods and Compositions for Brightening the Color of Thermally Processesd Nutritionals".
Abbott Pediatric Nutrition Product Guide 2011—"Similac Advance", pp. 16-19.

(56) References Cited

OTHER PUBLICATIONS

Bernstein et al., "Identification and Quantitation of Carotenoids and their Metabolites in the Tissues of the Human Eye," Exp. Eye Res 72:1-9 (2001).
Birch, et al., "A randomized controlled trial of early dietary supply of long-chain polyunsaturated fatty acids and mental development in term infants", Developmental Medicine and Child Neurology, vol. 42(3), pp. 174-181 (Mar. 2000).
Birch, et al., "Visual Maturation of Term Infants Fed Long-Chain Polyunsaturated Fatty Acid-Supplemented or Control Formula for 12 Mo." Am. J. Clin. Nutr. (2005), vol. 81, pp. 871-879.
Britton, George, "Structure and Properties of Carotenoids in Relation to Function," FASEB, vol. 9, pp. 1551-1558, Dec. 1995.
Canfield, Louise et al., "Red Palm Oil in the Maternal Diet Increases Provitamin A Carotenoids in Breastmilk and Serum of the Mother-Infant Dyad," Eur. Journal of Nutr. 40, pp. 30-38, 2001.
Cantrill, "Lutein from Tagetes erecta", Chemical and Technical Assessment (CTA) 63rd JECFA, FAO 2004 (5 pages), ftp://ftp.fao.org/es/esn/jecfa/cta/CTA_63_Lutein pdf.
"Carotino Fact Sheets from Carotino.com," http://www.carotino.com/carotenes1.html May 4, 2003.
Carlson, et al., "Visual acuity development in healthy preterm infants: effect of marine-oil supplementation," American Journal of Clinical Nutrition vol. 58(1), pp. 35-42 (1993).
Ermakov, et al., "Resonance Raman detection of carotenoid antioxidants in living human tissues," Optics Letters, vol. 26(15), pp. 1179-1181 (2001).
European Commission Report, "Report of the Scientific Committee on Food on the Revision of Essential Requirements of Infant Formulae and Follow-on Formulae," pp. 76-77 (May 18, 2003).
FSANZ "Standard 2.9.1" Infant Formula Products (Under Amendment No. 78) (2005-2006).
FSANZ "Standard 2.9.1" Infant Formula Products (Under Amendment No. 108) (May 28, 2009).
FDA—Infant Formula Act, Regulatory Information, Section 412 [21 USC Section 350(a)]; http://www.fda.gov/RegulatoryInformation/Legislation/FederalFoodDrugandCosmeticActFDCAct/FDCActChapterIVFood/ucm107864.htm, last accessed Nov. 2, 2011.
Forsyth, J.S. "Lipids and Infant Formulas," Nutrition Research Reviews (1998), vol. 11, pp. 255-278.
Gibson et al., "Dietary Fatty Acids in Growth and Development," Mal J. Nutr (2000) 6(2):171-179.
Greene, "How Much Milk Should My Baby Be Drinking?", Knol, (Jan. 18, 2001), http://knol.google.com/k/alan-greene/how-much-mild-should-my-baby-be-drinking/a2n7/wbik7op/1#, last visited Nov. 2, 2011.
Hata, et al., "Non-invasive raman spectroscopic detection of carotenoids in human skin", Journal of Investigative Dermatology, vol. 115(3), pp. 441-448 (2000).
Hoffman, et al., "Effects of supplementation with w3 long-chain polyunsaturated fatty acids on retinal and cortical development in premature infants", American Journal of Clinical Nutrition, vol. 57 (Suppl.), pp. 807S-812S (1993).
Hoffman, et al., "Visual Function in Breast-Fed Term Infants Weaned to Formula with or without Long-Chain Polyunsaturates at 4 to 6 months: A Randomized Clinical Trial;" J. Pediatr. 2003; 142:669-677.
Humphries et al., "Distribution of lutein, zexanthin, and related geometrical isomers in fruit, vegetables, wheat and pasta products," J. Agric. Food Chem, 51:1322-1327 (2003).
Inder et al., "Plasma vitamin A levels in the very low birthweight infant—relationship to respiratory outcome," Early Human Development 52 (1998), pp. 155-168.
Innis et al., "Docosahexaenoic acid and arachidonic acid enhance growth with no adverse effects in preterm infants fed formula," The Journal of Pediatrics (2002), vol. 140, No. 5, pp. 547-554.
Jewell et al., "A Comparison of Lutein and Zeaxanthin Concentrations in Formula and Human Milk Samples from Northern Ireland Mothers," European Journal of Clinical Nutrition, (2004) 58:90-97.

International Preliminary Report on Patentability for PCT/US06/41303 dated Apr. 29, 2008.
International Preliminary Report on Patentability for PCT/US07/87874 dated Jun. 30, 2009.
Office Action from U.S. Appl. No. 11/584,704 dated Mar. 4, 2009.
Office Action from U.S. Appl. No. 11/584,704 dated Nov. 12, 2009.
Office Action from U.S. Appl. No. 13/042,802 dated Jan. 20, 2012.
Office Action from U.S. Appl. No. 14/512,144 dated May 7, 2015.
Response in U.S. Appl. No. 14/512,144 dated Aug. 7, 2015.
Final Office Action in U.S. Appl. No. 14/512,144 dated Oct. 22, 2015.
Amendment and RCE in U.S. Appl. No. 14/512,144 dated Feb. 22, 2016.
Office Action in U.S. Appl. No. 14/512,144 dated Feb. 23, 2016.
Office Action in U.S. Appl. No. 14/512,144 dated Sep. 22, 2016.
Non Final Office Action for U.S. Appl. No. 11/646,671 dated Jun. 12, 2014.
Notice of Abandonment for U.S. Appl. No. 11/646,671 dated Jan. 29, 2015.
Office Action in Re-Examination Control No. 90/012,753 dated Jun. 4, 2013.
Response in Re-Examination Control No. 90/012,753 dated Aug. 5, 2013.
Office Action in Re-Examination Control No. 90/012,753 dated Feb. 25, 2014.
Amendment in Re-Examination Control No. 90/012,753 dated Apr. 24, 2014.
Statement of Grounds and Particulars in support of Notice of Opposition for AU Application No. 2006306366 dated Nov. 11, 2011.
First Examination Report for AU Application No. 2011238634 dated Oct. 10, 2012.
Office Action from Canadian Patent Application No. 2498973 dated Nov. 17, 2011.
Office Action from Canadian Patent Application No. 2498973 dated Jun. 16, 2014.
Office Action for Canadian Patent Application No. 2,747,281 dated May 29, 2012.
Office Action for Canadian Patent Application No. 2,747,281 dated Apr. 2, 2012.
Office Action for Canadian Patent Application No. 2,747,281 dated Dec. 3, 2012.
Final Office Action for CA Patent Appl. No. 2,747,281 dated Aug. 26, 2014.
Summary for Reasons of Rejection of an Application for CA Patent Application No. 2,747,281 dated Oct. 6, 2015.
Office Action for CN Application No. 200680039665.7 dated Apr. 13, 2011.
Second Office Action for CN Application No. 200680039665.7 dated Apr. 12, 2012.
First Office Action for CN Application No. 201310096170.x dated Jan. 10, 2014.
Second Office Action for CN Application No. 201310096170.x dated Aug. 1, 2014.
Third Office Action for CN Application No. 201310096170.x dated Feb. 5, 2015.
Office Action from Colombian Application No. 08037363 dated May 19, 2012.
Official Denial from Costa Rican Application No. 9888 dated Dec. 20, 2016.
Office Action from EG Application No. 670/2008 dated Nov. 2, 2012.
Office Action for EP Application No. 06826479.5 dated Apr. 7, 2011.
Communication pursuant to Article 94(3) for EP Application No. 06826479.5 dated Oct. 21, 2008.
Summons to attend oral proceedings for EP Application No. 06826479.5 dated Mar. 30, 2012.
Response to Exam Report and Summons to attend oral proceedings for EP Application No. 06826479.5 dated May 21, 2012.
Decision to Refuse EP Patent Application No. 06826479.5 dated Oct. 26, 2012.

(56) References Cited

OTHER PUBLICATIONS

Notice of Appeal in EP Application No. 06826479.5 dated Dec. 13, 2012.
Grounds in Support of Appeal in EP Application No. 06826479.5 dated Feb. 26, 2013.
Summons to attend oral proceedings for EP Application No. 06826479.5 dated Apr. 2, 2014.
Response to Summons to attend oral proceedings for EP Application No. 06826479.5 dated Jul. 7, 2014.
Communication from Board of Appeal for EP Application No. 06826479.5 dated Jul. 23, 2014.
Response to Communication from Board of Appeal for EP Application No. 06826479.5 dated Sep. 9, 2014.
Appeal Decision in EP Application No. 06826479.5 dated Nov. 7, 2014.
Intention to Grant in EP Application No. 06826479.5 dated Apr. 30, 2015.
Decision to Grant in EP Application No. 06826479.5 dated Sep. 24, 2015.
Notice of Opposition against EP1945045B1 by Nestec SA dated Jul. 20, 2016.
Opponent's Written Submissions in Preparation for Oral Proceedings dated Aug. 25, 2017.
Notice of Opposition against EP2283736 by Nestec SA dated Feb. 28, 2019.
Wyeth Nutrition—Master Formulation document describing the composition of SMA LBW ready to feed infant formula, Jun. 2003.

* cited by examiner

INFANT FORMULAS CONTAINING DOCOSAHEXAENOIC ACID AND LUTEIN

CROSS-REFERENCE TO RELATED APPLICATIONS

This application is a continuation of U.S. patent application Ser. No. 14/512,144, filed Oct. 10, 2014, now U.S. Pat. No. 9,861,120, which is a continuation of U.S. patent application Ser. No. 11/646,671, filed Dec. 28, 2006, which is a continuation-in-part of U.S. patent application Ser. No. 11/584,704, filed Oct. 20, 2006, now U.S. Pat. No. 7,829,126, which claims priority to and the benefit of U.S. Provisional Patent Application 60/730,283 filed Oct. 26, 2005.

TECHNICAL FIELD

The present invention relates to infant formulas and methods for using those formulas to promote retinal health and vision development in infants, including reducing the severity or risk of retinopathy of prematurity.

BACKGROUND

Infant formulas are commonly used today to provide supplemental or sole source nutrition early in life. These formulas contain protein, carbohydrate, fat, vitamins, minerals, and other nutrients. They are commercially available as powders, ready-to-feed liquids, and liquid concentrates.

Although many infant formulas provide a quality alternative to human milk, they still do not provide the same high level of nutrition as found in human milk. As such, much of the research effort into infant formulas over the past several years has been directed to better understanding the natural constituents of human milk, and then modifying infant formulas accordingly, or at least to the extent possible with currently available technology.

Arachidonic acid and docosahexaenoic acid, for example, have been identified in human milk and subsequently added to synthetic infant formulas. These fatty acids support brain and vision development in infants, and are now commonly found in commercially available formulas such as Similac® Advance® Infant Formula, Isomil® Advance® Infant formula, and Similac® Special Care® Advance® infant formula, all of which are available from Ross Products Division, Abbott Laboratories, Columbus, Ohio, USA.

Lutein has also been identified in human milk. Although it is not currently added to infant formulas as an isolated ingredient, lutein can be found at low concentrations in infant formulas as an inherent ingredient in some of the natural oils commonly used to make such formulas. Lutein is an antioxidant that also happens to concentrate within the retina of the eye. It is generally known that dietary lutein may provide individuals with eye health benefits, and it is speculated that such benefits may be extended to infants receiving lutein from either human milk or supplemented infant formula.

It is now believed that a combination of lutein and docosahexaenoic acid may be particularly important in promoting retinal health and vision development in infants. Both materials are present in human milk and both are known to concentrate in the retina in otherwise healthy subjects. Docosahexaenoic acid (DHA), as a polyunsaturated fatty acid, is highly susceptible to damage by oxidation and degradation within the eye, while lutein is a known antioxidant. It is believed that by adding lutein to infant formulas, not only will it concentrate within the retina, it may also reduce oxidative degradation of the retinal DHA and thus further promote retinal health and vision development in the infant.

It has now been found, however, that lutein concentrations in infant formula must be much higher than the lutein concentrations found in human milk in order to achieve the same plasma lutein concentrations found in breast fed infants due to a lower relative bioavailability of lutein from infant formula. Although infant formulas today typically contain less than about 20 mcg/liter of lutein, most of which comes inherently from added fats and oils, it has now been found that such lutein concentrations must exceed about 50 mcg/liter, preferably from about 100 mcg/liter to about 200 mcg/liter, in order to duplicate plasma lutein concentrations found in exclusively breast fed infants.

Consequently, it has also been found that infant formulas containing combinations of lutein and DHA, as described above, should now be formulated with higher ratios (lutein to DHA) than are commonly found in human milk. These weight ratios of lutein (mcg) to DHA (mg) should now range from about 1:2 to about 10:1.

It has also been found that the severity or risk of retinopathy of prematurity (ROP) is influenced by skin carotenoid levels found in preterm infants fed human milk. This finding suggests that preterm infants can be monitored for skin carotenoid concentrations, and then for those infants demonstrating low skin carotenoid levels, supplemental carotenoids may be administered in amounts sufficient to increase skin carotenoid levels, to thus reduce the risk or severity of retinopathy of prematurity.

SUMMARY

A first embodiment is a method of reducing the risk or severity of retinopathy of prematurity in preterm infants. The method comprises (a) measuring skin carotenoid levels in preterm infants, preferably by Raman Spectroscopy, and then (b) administering supplemental carotenoids to those infants in need thereof, wherein the supplemental carotenoids comprise lutein, lycopene, beta-carotene, and zeaxanthin. The supplemental carotenoids may be provided by an infant formula comprising, on a ready-to-feed basis, from about 100 to about 2000 mcg/liter of total carotenoids, wherein the total carotenoids include at least about 50 mcg/liter of lutein.

The supplemental carotenoids may also be administered as a preterm infant formula comprising fat, protein, carbohydrate, vitamins, and minerals. The infant formula may further comprise docosahexaenoic acid in a weight ratio of lutein (mcg) to docosahexaenoic acid (mg) of from about 1:2 to about 10:1.

It has been found that the severity or risk of retinopathy of prematurity (ROP) is influenced by skin carotenoid levels found in preterm infants fed human milk. This finding suggests that skin carotenoid levels may be monitored in preterm infants, and then administered to those infants in need thereof to reduce the risk or severity of retinopathy of prematurity.

It has been found that infant formulas may be prepared with lutein concentrations of at least 50 mcg/liter if they are to produce the same plasma lutein concentrations found in breast fed infants, even though human milk itself typically contains no more than about 30 mcg/liter of lutein. It has also been found, consequently, that the weight ratio of lutein (mcg) to DHA (mg) in an infant formula may range from about 1:2 to about 10:1. It is believed that the combination of lutein and docosahexaenoic acid are particularly useful in promoting retinal health and vision development in infants, provided that sufficient quantities of each are designed into the infant formula as described herein.

DETAILED DESCRIPTION

Figure 1:
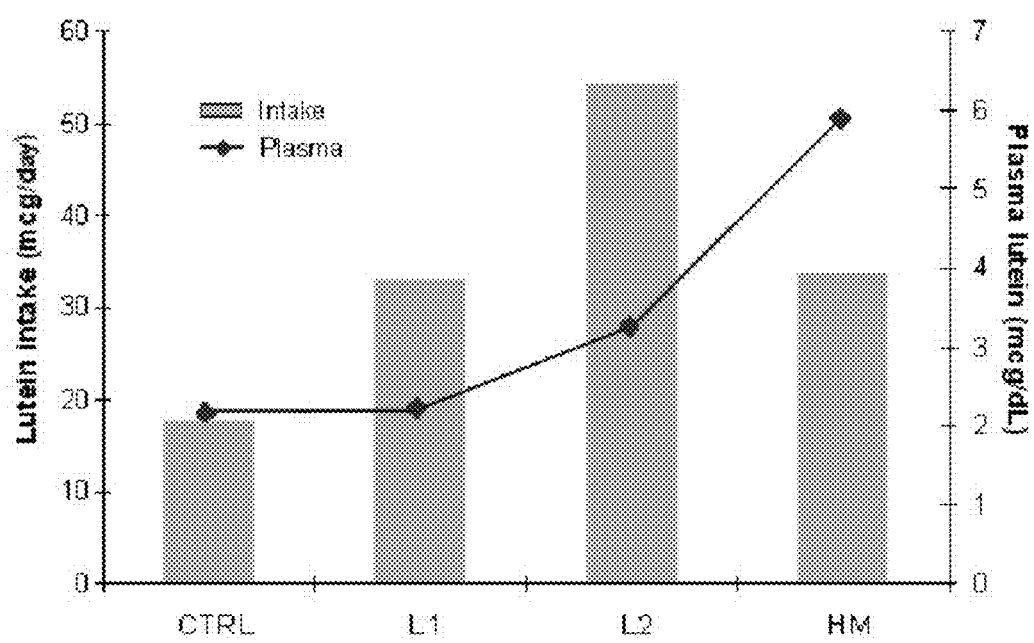
FIG. 1 is a graph of lutein intake (mcg/day) and corresponding plasma lutein concentrations (mcg/dl) in infant groups fed human milk (HM) or infant formulas containing varied concentrations of lutein [CTRL with 14.6 mcg lutein/liter (no added lutein, all lutein inherent in ingredients)]; L1 with 32.6 mcg lutein/liter (approximately 18 mcg/liter added lutein, remainder inherent), L2 with 52.6 mcg lutein/liter (approximately 38 mcg/liter added lutein, remainder inherent).
Figure 2:
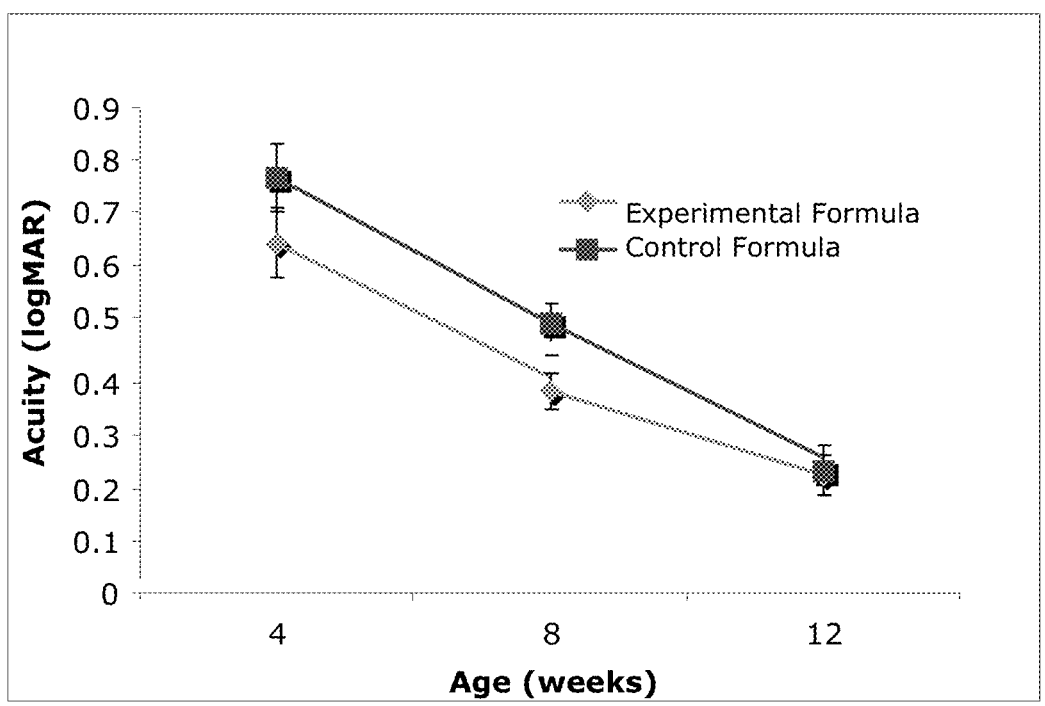
FIG. 2 is a graph showing visual acuity as measured by sweep visual evoked potential (logMAR) in monkeys at 4, 8, and 12 weeks of age. The monkeys are fed infant formula with either DHA and added lutein (n=8) or DHA without added lutein (n=8) during a 12 week feeding period.

The present invention, including essential and some optional features or limitations, is described hereinafter in detail.

The terms "infant" and "preterm infant" as used herein, unless otherwise specified, are used interchangeably to mean preterm infants born at less than about 37 weeks gestation, typically from about 26 to about 34 weeks gestation, and or low birth weight infants (term or preterm) at less than 2.5 kg at birth, including those less than 1.8 kg at birth.

The term "infant formula" as used herein, unless otherwise specified, refers to a nutritional composition, typically free of egg phospholipids, that is designed for infants and contains sufficient protein, carbohydrate, fat, vitamins, and minerals to potentially serve as the sole source of nutrition when provided in sufficient quantity.

The term "ready-to-feed" as used herein, unless otherwise specified, refers to infant formulas in liquid form suitable for administration to an infant, including reconstituted powders, diluted concentrates, and manufactured liquids.

As used herein, all concentrations expressed as either "mcg/liter" or "mg/liter" refer to ingredient concentrations within the described infant formulas as calculated on a ready-to-feed or as fed basis, unless otherwise specified.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The infant formulas and methods described herein may also be substantially free of any optional or selected essential ingredient or feature described herein, provided that the remaining formula still contains all of the required ingredients or features as described herein. In this context, the term "substantially free" means that the selected composition contains less than a functional amount of the optional ingredient, typically less than 0.1% by weight, and also including zero percent by weight of such optional or selected essential ingredient.

The methods of the present invention may comprise, consist of, or consist essentially of the essential elements and limitations of the invention described herein, as well as any additional or optional ingredients, components, or limitations described herein or otherwise useful in nutritional formula applications.

Method of Use

A first embodiment of the present invention is a method of reducing the risk or severity of retinopathy of prematurity in preterm infants. The method comprises (a) measuring skin carotenoid levels in preterm infants, preferably by Raman Spectroscopy, and then (b) administering supplemental carotenoids to those infants in need thereof, wherein the supplemental carotenoids comprise lutein, lycopene, beta-carotene, and zeaxanthin. The supplemental carotenoids may be provided by an infant formula comprising, on an as-fed basis, up to about 2000 mcg/liter of total carotenoids, wherein the total carotenoids include at least about 50 mcg/liter of lutein.

The term "supplemental carotenoids" as used herein, unless otherwise specified, means a carotenoid blend comprising up to about 2000 mcg/liter, including from about 50 to about 1500 mcg/liter, and also including from about 100 to about 1200 mcg/liter, of total carotenoids, wherein the total carotenoids comprise beta-carotene, lycopene, zeaxanthin, and lutein, which includes at least about 50 mcg/liter of lutein, including from about 50 to about 1150 mcg/liter, also including from about 75 to about 230 mcg/liter, and also including from about 100 to about 200 mcg/liter.

This particular method may therefore provide the infant with an effective amount of lutein to provide the stated benefits, including from about 7 to about 300 mcg/kg/day, including from about 14 to about 220 mcg/kg/day, and also including from about 22 to about 150 mcg/kg/day (of lutein per kg of body weight of the infant).

All lutein and carotenoid concentrations and ratios referenced herein are calculated on a free lutein or carotenoid basis, unless otherwise specified.

The supplemental carotenoids may also be administered alone or in combination with other ingredients as a preterm infant formula comprising fat, protein, carbohydrate, vitamins, and minerals. The infant formula may further comprise docosahexaenoic acid in a weight ratio of lutein (mcg) to docosahexaenoic acid (mg) of from about 1:2 to about 10:1, including from about 1.5:1 to about 9:1, also including from about 1.7:1 to about 5:1.

When supplemental carotenoids are administered in the form of a preterm infant formula, that formula may be prepared and administered as a sole source, primary source, or supplemental source of nutrition.

Eye and vision development occurs at a rapid rate during the first year of life. At birth, infants can only see high-contrast objects at perhaps 25-30 cm away. During the next 6 months, the infant's retina develops enough to see and discern small details. And as an infant's vision develops, most of which will occur during the first year, the infant becomes better able to learn through visual stimulation now made possible with a newly developed sight. For infants, this visual learning then plays a key role in brain and cognitive development, especially during the first 2-3 years of life.

By promoting retinal health and vision development in infants, the infant formulas of the present invention may also help children develop their ability to visually learn as soon as possible, and to potentially accelerate brain and cognitive development associated with early visual stimulation through the developing retina of the eye. The infant formulas described herein are therefore useful in promoting vision development in infants, and consequently are useful in promoting secondary benefits such as associated cognitive and brain development through early visual stimulation. It is also useful in preterm infants to help accelerate the development of normal vision, to thus reduce the time needed to catch-up with development milestones set by their term infant counterparts.

The methods described herein are particularly useful to reduce the risk or severity of retinopathy of prematurity. This condition often affects preterm infants and is most commonly characterized by abnormal development of retinal vessels in the eye possibly as a result of oxidative stress secondary to high oxygen tension. This affliction can occur to varying degrees, from slight vessel involvement with minimal or no impact on vision, to partial or complete retinal detachment leading to blindness. Historically, therapy for appropriate cases included laser treatment as well as cryotherapy.

In accordance with the methods herein, the supplemental carotenoids may be administered to those infants with a measured Raman Count of less than about 20,000, including from about 100 to about 15,000, also including from about 400 to about 10,000, wherein all such ranges are proceeded by administration of supplemental carotenoids in amounts sufficient to increase the Raman Count in the infant, typically by at least about 5%, including from about 20% to about 500%. Raman counts correlate with serum and tissue carotenoid levels.

Carotenoids

The supplement carotenoids for us herein—lutein, lycopene, beta-carotene, and zeaxanthin—may be provided or otherwise administered in any form suitable for use in preterm infants.

The term "lutein" as used herein, unless otherwise specified, refers to one or more of free lutein, lutein esters, lutein salts, or other lutein derivatives or related structures as described or otherwise suggested herein. Lutein or lutein sources suitable for use in the infant formulas of the present invention include free lutein as well as esters, salts or other derivatives or related structures thereof, including those that conform to the formula:

cis and trans isomers. The $R_1$ and $R_2$ moieties are residues of a saturated or unsaturated $C_1$ to $C_{22}$ fatty carboxylic acids, non-limiting examples of which include formic, acetic, propionic, butyric, valeric, caproic, caprylic, capric, lauric, myristic, palmitic, stearic, and oleic acids.

Lutein for use herein includes any natural or synthetic source that is known for or is otherwise an acceptable source for use in oral nutritionals, including infant formulas. Lutein sources can be provided as individual ingredients or in any combination with other materials or sources, including sources such as multivitamin premixes, mixed carotenoid premixes, pure lutein sources, and inherent lutein from other fat or oil components in the infant formula. The lutein concentrations and ratios as described herein are calculated based upon added and inherent lutein sources. The infant formulas of the present invention preferably comprise at least about 25%, more preferably from about 50% to about 95%, by weight of total lutein as added lutein, the remainder being inherent lutein that accompanies added fats and oils.

Each of the carotenoids for use herein may be obtained from any known or otherwise suitable material source for use in infant nutritional formulas, and each can be provided individually, or all together, or in any combination and from any number of sources, including sources such as multivitamin premixes containing other vitamins or minerals in combination with one or more of the other carotenoids as described herein. Non-limiting examples of some suitable sources include LycoVit® synthetic lycopene dispersion in vegetable oil provided by BASF, Mount Olive, N.J., USA, Lyc-O-Mato® tomato extract in oil, powder, or bead form provided by LycoRed Natural Products Industries, Ltd., Bear Sheba, Israel, water-dispersible and oil soluble lycopene provided by DSM Nutritional Products, Basel, Switzerland, FloraGLO® brand free lutein provided by Kemin Foods, Des Moines, Iowa, Xangold Lutein Esters provided by Cognis, Cincinnati, Ohio, U.S.A., and beta-carotene provided by BASF, Mount Olive, N.J.

Non-limiting examples of some suitable lutein sources for use herein include FloraGLO® Crystalline Lutein, available from Kemin Foods, Des Moines, Iowa, USA; and Xangold Lutein Esters provided by Cognis, Cincinnati, Ohio, USA.

The infant formulas for use herein include those comprising a single source combination of free lutein and zeaxanthin, in a purified crystalline extract from the marigold flower (*Tagetes erecta*), wherein the free lutein represents from 85% to 95% by weight of the combination and the

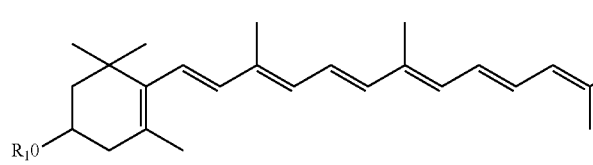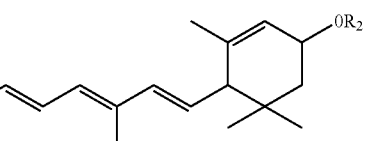

The above formula includes the general structure of lutein and related derivatives or structures. Free lutein, for example, corresponds to the formula wherein $R_1$ and $R_2$ are both hydrogen, and includes cis and trans isomers thereof as well as salts thereof, e.g., sodium, potassium.

Lutein esters suitable for use herein include any lutein ester of the above formula wherein $R_1$ and $R_2$ are the same or different, and are nutritionally acceptable monovalent salts, hydrogen or an acyl residue of a carboxylic acid, provided that at least one of $R_1$ or $R_2$ is an acyl residue of a carboxylic acid. Suitable lutein esters include, as well, both zeaxanthin represents from about 5% to about 15% by weight of the combination. A lutein-zeaxanthin combination is available from Kemin Foods, Des Moines, Iowa, USA, under the FloraGLO® brand.

Docosahexaenoic Acid (DHA)

The infant formulas for use herein may comprise docosahexaenoic acid, an organic carboxylic acid having a chain length of 22 carbons with 6 double bonds beginning with the third carbon from the methyl end (22:6 n-3). Any source of docosahexaenoic acid is suitable for use herein provided that such a source is also known for or otherwise suitable for use in infant formulas and is compatible with the other selected ingredients in the formula.

Docosahexaenoic acid concentrations in the infant formulas may be selected so that the resulting weight ratio of lutein to docosahexaenoic acid falls within the range as defined herein. Such concentrations most typically range from about 36 to 360 mg/liter, including from about 50 to about 144 mg/liter, and also including from about 72 to about 130 mg/liter, as calculated on a ready-to-feed basis.

The docosahexaenoic acid may be added to the infant formula as free fatty acids or as compounds or materials that can otherwise provide a source of such free fatty acids upon or following administration to the infant, including non-egg phospholipids and glyceride esters (mono-, di-, tri-) of docosahexaenoic acids. Polyunsaturated fatty acids and sources thereof are described in U.S. Pat. No. 6,080,787 (Carlson, et al.) and U.S. Pat. No. 6,495,599 (Auestad, et al.), which descriptions are incorporated by reference herein. Some non-limiting examples of suitable docosahexaenoic acid sources include fish oils, algal oils, other single cell oils, and combinations thereof.

The infant formulas may further comprise, in addition to the docosahexaenoic acid as described herein, other long chain polyunsaturated fatty acids such as arachidonic acid (20:4 n-6), eicosapentaenoic acid or EPA (20:5 n-3), linoleic acid (18:2 n-6), γ-linolenic acid or GLA (18:3 n-6), α-linolenic acid (18:3 n-3), dihomo-γ-linolenic or DHGLA (20:3 n-6), α-linolenic (18:3 n-3), stearidonic acid (18:4 n-3), and combinations thereof. Such optional long chain polyunsaturated fatty acids may likewise be formulated into the infant formula as free fatty acids or as compounds or materials that can otherwise provide a source of such free fatty acids upon or following administration to the infant, including non-egg phospholipids and glyceride esters (mono-, di-, tri-) of docosahexaenoic acids.

Other Nutrients

The infant formulas for use herein may comprise fat, protein, carbohydrate, minerals, and vitamins, all of which are selected in kind and amount to meet the dietary needs of the intended infant population.

Many different sources and types of carbohydrates, fats, proteins, minerals and vitamins are known and can be used in the infant formulas, provided that such nutrients are compatible with the added ingredients in the selected formulation and are otherwise suitable for use in an infant formula.

Carbohydrates suitable for use herein may be simple or complex, lactose-containing or lactose-free, or combinations thereof, non-limiting examples of which include hydrolyzed, intact, naturally and/or chemically modified cornstarch, maltodextrin, glucose polymers, sucrose, corn syrup, corn syrup solids, rice or potato derived carbohydrate, glucose, fructose, lactose, high fructose corn syrup and indigestible oligosaccharides such as fructooligosaccharides (FOS), galactooligosaccharides (GOS), and combinations thereof.

Proteins suitable for use herein include hydrolyzed, partially hydrolyzed, and non-hydrolyzed or intact proteins or protein sources, and can be derived from any known or otherwise suitable source such as milk (e.g., casein, whey), animal (e.g., meat, fish), cereal (e.g., rice, corn), vegetable (e.g., soy), or combinations thereof.

Proteins for use herein may also include, or be entirely or partially replaced by, free amino acids known for or otherwise suitable for use in infant formulas, non-limiting examples of which include alanine, arginine, asparagine, carnitine, aspartic acid, cystine, glutamic acid, glutamine, glycine, histidine, isoleucine, leucine, lysine, methionine, phenylalanine, proline, serine, taurine, threonine, tryptophan, taurine, tyrosine, valine, and combinations thereof. These amino acids are most typically used in their L-forms, although the corresponding D-isomers may also be used when nutritionally equivalent. Racemic or isomeric mixtures may also be used.

Fats suitable for use in the infant formulas include coconut oil, soy oil, corn oil, olive oil, safflower oil, high oleic safflower oil, algal oil, MCT oil (medium chain triglycerides), sunflower oil, high oleic sunflower oil, palm and palm kernel oils, palm olein, canola oil, marine oils, cottonseed oils, and combinations thereof.

Vitamins and similar other ingredients suitable for use in the infant formulas include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

Minerals suitable for use in the infant formulas include calcium, phosphorus, magnesium, iron, zinc, manganese, copper, chromium, iodine, sodium, potassium, chloride, and combinations thereof.

The infant formulas preferably comprise nutrients in accordance with the relevant infant formula guidelines for the targeted consumer or user population, an example of which would be the Infant Formula Act, 21 U.S.C. Section 350(a).

Infant formulas for use herein may comprise the carbohydrate, fat, and protein concentrations described in the following table.

TABLE 1

Infant Formula Nutrients[1]

| Nutrient | Range | gm/100 kcal | gm/liter[2] |
|---|---|---|---|
| Carbohydrate | 1$^{st}$ embodiment | 8-16 | 54-108 |
|  | 2$^{nd}$ embodiment | 9-13 | 61-88 |
| Fat | 1$^{st}$ embodiment | 3-8 | 20-54 |
|  | 2$^{nd}$ embodiment | 4-6.6 | 27-45 |
| Protein | 1$^{st}$ embodiment | 1-3.5 | 7-24 |
|  | 2$^{nd}$ embodiment | 1.5-3.4 | 10-23 |

[1]All numerical values may be modified by the term "about"
[2]From ready-to-feed liquid, reconstituted powder, or diluted concentrate The infant formulas for use herein may include those formulas that comprise per 100 kcal of formula one or more of the following: vitamin A (from about 250 to about 750 IU), vitamin D (from about 40 to about 100 IU), vitamin K (greater than about 4 mcg), vitamin E (at least about 0.3 IU), vitamin C (at least about 8 mg), thiamine (at least about 8 g), vitamin B12 (at least about 0.15 g), niacin (at least about 250 g), folic acid (at least about 4 g), pantothenic acid (at least about 300 g), biotin (at least about 1.5 g), choline (at least about 7 mg), and inositol (at least about 4 mg).

These infant formulas may also comprise per 100 kcal of formula one or more of the following: calcium (at least about 50 mg), phosphorus (at least about 25 mg), magnesium (at least about 6 mg), iron (at least about 0.15 mg), iodine (at least about 5 g), zinc (at least about 0.5 mg), copper (at least about 60 g), manganese (at least about 5 g), sodium (from about 20 to about 60 mg), potassium (from about 80 to about 200 mg), and chloride (from about 55 to about 150 mg).

Optional Ingredients

The infant formulas for use herein may further comprise other optional ingredients that may modify the physical, chemical, aesthetic or processing characteristics of the compositions or serve as pharmaceutical or additional nutritional components when used in the targeted infant population. Many such optional ingredients are known or are otherwise suitable for use in nutritional products and may also be used in the infant formulas for use herein, provided that such optional materials are compatible with the essential materials described herein and are otherwise suitable for use in an infant formula.

Non-limiting examples of such optional ingredients include preservatives, additional anti-oxidants, emulsifying agents, buffers, colorants, flavors, nucleotides and nucleosides, probiotics, prebiotics, lactoferrin and related derivatives, thickening agents and stabilizers, and so forth.

Product Form

The infant formulas for use herein may be prepared as any product form suitable for use in infants, including reconstitutable powders, ready-to-feed liquids, and dilutable liquid concentrates, which product forms are all well known in the nutrition and infant formula arts.

The infant formulas for use herein may have any caloric density suitable for the intended infant population, or provide such a density upon reconstitution of a powder embodiment or upon dilution of a liquid concentrate embodiment. Most caloric densities are at least about 18 kcal/fl oz (609 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-30 kcal/fl oz, most typically from about 22-24 kcal/fl oz, formulas are more commonly used in pre-term of low birth weight infants, and the 20-21 kcal/fl oz (675-680 to 700 kcal/liter) formulas are more often used in term infants. Higher caloric feedings may be used with pre-term infants of low birth weight; such feedings are typically from about 27 kcal/fl oz (90-95 kcal/liter) to about 30 kcal/fl oz (1000-1015 kcal/liter).

For powder infant formulas for use herein, such powders are typically in the form of flowable or substantially flowable particulate compositions, or at least particulate compositions that can be easily scooped and measured with a spoon or similar other device, wherein the compositions can easily be reconstituted by the intended user with a suitable aqueous fluid, typically water, to form a liquid nutritional formula for immediate oral or enteral use. In this context, "immediate" use generally means within about 48 hours, most typically within about 24 hours, preferably right after reconstitution. These powder embodiments include spray dried, agglomerated, dry mixed or other known or otherwise effective particulate form. The quantity of a nutritional powder required to produce a volume suitable for one serving can vary.

The infant formulas for use herein may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

Method of Manufacture

The infant formulas for use herein may be prepared by any known or otherwise effective technique suitable for making and formulating an infant formula or similar other formula, variations of which may depend upon variables such as the selected product form, ingredient combination, packaging and container selection, and so forth, for the desired infant formula. Such techniques and variations for any given formula are easily determined and applied by one of ordinary skill in the infant nutrition formulation or manufacturing arts.

The infant formulas for use herein, including the exemplified formulas described hereinafter, can therefore be prepared by any of a variety of known or otherwise effective formulation or manufacturing methods. These methods most typically involve the initial formation of an aqueous slurry containing carbohydrates, proteins, lipids, stabilizers or other formulation aids, vitamins, minerals, or combinations thereof. The slurry is emulsified, pasteurized, homogenized, and cooled. Various other solutions, mixtures, or other materials may be added to the resulting emulsion before, during, or after further processing. This emulsion can then be further diluted, heat-treated, and packaged to form a ready-to-feed or concentrated liquid, or it can be heat-treated and subsequently processed and packaged as a reconstitutable powder, e.g., spray dried, dry mixed, agglomerated.

Other suitable methods for making nutritional formulas are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application 20030118703 A1 (Nguyen, et al.), which descriptions are incorporated herein by reference.

Experiment

The purpose of this experiment is to evaluate changes in visual acuity in animals fed infant formulas comprising either DHA or DHA with added lutein. Sixteen monkeys are fed one of two defined infant formulas during their first 12 weeks of life. One is a control formula—Similac® Advance® Infant formula, available from Abbott Laboratories, Columbus Ohio, and the other is an experimental formula including Similac® Advance® Infant Formula as a base, but with added carotenoids comprising lutein. The formulas include the following:

| Nutrient | Control formula | Experimental formula |
|---|---|---|
| DHA | 50 mg/L | 60 mg/L |
| Lutein | 0 mcg/L added (18 mcg/L inherent) | 117 mcg/L |
| Zeaxanthin | 0 mcg/L added (4 mcg/L inherent) | 36 mcg/L |
| Zeaxanthin/lutein | 22% | 31% |

The base formula (Similac® Advance® Infant formula) contains water, nonfat milk, lactose, high oleic safflower oil, soy oil, coconut oil, whey protein concentrate; C. cohnii oil, M. alpina oil, potassium citrate, calcium carbonate, ascorbic acid, mono- and diglycerides, soy lecithin, carrageenan, potassium chloride, magnesium chloride, sodium chloride, ferrous sulfate, choline chloride, choline bitartrate, taurine, m-inositol, d-alpha-tocopheryl acetate, L-carnitine, zinc sulfate, niacinamide, calcium pantothenate, riboflavin, vitamin A palmitate, cupric sulfate, thiamine chloride hydrochloride, pyridoxine hydrochloride, beta-carotene, folic acid, manganese sulfate, phylloquinone, biotin, sodium selenate, vitamin D3, cyanocobalamin and nucleotides (adenosine 5'-monophosphate, cytidine 5'-monophosphate, disodium guanosine 5'-monophosphate, disodium uridine 5'-monophosphate).

The monkeys are randomized to receive either the experimental (n=8) or control (n=8) formulas from birth to 12 weeks of life. The animals do not receive any milk from their mothers. Infants and mothers are separated at birth. During the study, the monkeys are exposed to light having the intensity and spectral characteristics of sunlight for 12 hours per day to simulate the light-induced oxidative stress potentially experienced by infants. During the study, the monkeys are evaluated for several parameters, including plasma lutein concentrations and sweep visual evoked potential (VEP).

Plasma Lutein

Plasma concentrations of lutein, lycopene, and beta-carotene are not significantly different between the monkeys fed the control and experimental formulas at birth (0 weeks of age). Plasma lutein concentrations are significantly higher in monkeys fed the experimental formula than monkeys fed the control formula at 4 ($p<0.001$), 8 ($p<0.001$), and 12 ($p<0.001$) weeks of age. Similarly, plasma lycopene concentrations are significantly higher in the experimental group compared to the control group at 4 ($p<0.001$), 8 ($p<0.001$), and 12 ($p<0.001$) weeks. Plasma beta-carotene concentrations are significantly greater in the experimental formula group than the control formula group at 4 ($p=0.005$) and 8 ($p=0.010$), but not 12 ($p=0.052$) weeks of age.

Visual Acuity

The monkeys are assessed for changes in visual acuity at 4, 8, and 12 weeks of life. Visual acuity is measured by sweep visual evoked potential (VEP), a method well known in the art for measuring visual evoked potential in infants. Visual acuity is measured by determining the smallest spatial frequency high contrast grating that evokes a measurable response from the visual cortex. The VEP from the primary cortical visual area is recorded using small silver disk EEG electrodes placed on the scalp with water-soluble electrode paste. The infant is held in an experimenter's lap while it gazes at a video monitor displaying phase-reversing black and white gratings. When necessary, the infant's attention will be drawn to the center of the screen with small dangling toys. During each "sweep", the spatial frequency of the grating will be decreased stepwise from above to below the subject's acuity threshold during a recording period of several seconds. The amplitude of the second harmonic of the VEP response, which reflects the response linked to the stimulus reversal rate, will be plotted as a function of spatial frequency to define the subject's acuity threshold (Neuringer M, Jeffrey B G: Visual development: neural basis and new assessment methods. *J Pediatr* 2003; 143:S87-S95).

VEP scores from the study are summarized in the FIG. 1 graph. Lower VEP (logMAR) scores are indicative of better visual acuity. Although VEP scores decreased (i.e., visual acuity improved) for all monkeys during the 12 week testing period, as expected, the VEP scores at 8 weeks were surprisingly lower in the experimental group (added lutein+DHA formula) than in the control group (DHA without added lutein formula) (4 weeks, $p=0.412$, etc.)

The data suggest accelerated development in infant monkeys fed the experimental formula at 8 weeks of life— specifically in visual acuity as measured by VEP values. To extrapolate the data to human infants, the eye development in monkeys at ages of 4, 8, and 12 weeks corresponds to the eye development in human infants at 4, 8, and 12 months, respectively. The data therefore suggests that even in a human infant, the experimental formula would improve visual acuity at between about 4 and about 12 months of life.

EXAMPLES

The following examples represent specific formulas for use in the methods defined herein, each of which is given solely for the purpose of illustration and is not to be construed as limitations of the present invention, as many variations thereof are possible without departing from the spirit and scope of the invention. All exemplified amounts are weight percentages based upon the total weight of the composition, unless otherwise specified.

Examples 1.1-1.3

The following are examples of milk-based, ready-to-feed, infant formulas suitable for use in the skin carotenoid methods.

| Ingredient | Example 1.1 Amount per 454 kg | Example 1.2 Quantity per 454 kg | Example 1.3 Quantity per 454 kg |
|---|---|---|---|
| Water | QS | QS | QS |
| Lactose | 27 kg | 27 kg | 27 kg |
| ARA-containing oil (40% ARA) | 0.167 kg | 0.167 kg | 0.167 kg |
| DHA-containing oil (40% DHA) | 0.063 kg | 0.095 kg | 0.145 kg |
| Non-fat dry milk | 11.33 kg | 11.33 kg | 11.33 kg |
| High oleic safflower oil | 6.5 kg | 6.5 kg | 6.5 kg |
| Mono- and di-glycerides | 0.162 kg | 0.162 kg | 0.162 kg |
| Soybean oil | 5 kg | 5 kg | 5 kg |
| Whey protein | 2.8 kg | 2.8 kg | 2.8 kg |
| Calcium carbonate | 0.211 kg | 0.211 kg | 0.211 kg |
| Coconut oil | 4.6 kg | 4.6 kg | 4.6 kg |
| Citric acid | 0.014 kg | 0.014 kg | 0.014 kg |
| Potassium citrate | 0.245 kg | 0.245 kg | 0.245 kg |
| Ascorbic acid | 178 g | 178 g | 178 g |
| Lecithin | 162 g | 162 g | 162 g |
| Magnesium chloride | 25 g | 25 g | 25 g |
| Potassium chloride | 88 g | 88 g | 88 g |
| Ferrous sulfate | 26 g | 26 g | 26 g |
| Carrageenan | 136 g | 136 g | 136 g |
| Choline chloride | 25 g | 25 g | 25 g |
| Nucleotide and choline premix[3] | 133 g | 133 g | 133 g |
| Riboflavin | 1 g | 1 g | 1 g |
| L-Carnitine | 1.5 g | 1.5 g | 1.5 g |
| Potassium hydroxide | 998 g | 998 g | 998 g |
| Water soluble vitamin premix[1] | 65 g | 65 g | 65 g |
| Vitamin ADEK premix[2] | 21 g | 21 g | 21 g |
| Vitamin A | 0.4 g | 0.4 g | 0.4 g |
| Added carotenoids[4] | —[4] | —[4] | —[4] |
| Total carotenoids[4] | 186 | 400 | 555 |
| Total Lutein w/ zeaxanthin (mcg/L)[5] | 90 | 150 | 200 |
| Total lycopene | 30 | 90 | 135 |
| Total beta carotene | 66 | 160 | 220 |
| Total DHA (mg/liter) | 50 | 75 | 115 |

[1]premix contains (per 65 g) 19.8 g taurine, 14.4 g inositol, 6.7 g zinc sulfate, 4.2 g niacinamide, 2.6 g calcium pantothenate, 2.3 g ferrous sulfate, 0.8 g cupric sulfate, 0.6 g thiamine, 0.3 g riboflavin, 0.26 g pyridoxine, 0.1 g folic acid, 0.07 g manganese sulfate, 0.03 g biotin, 0.025 g sodium selenate, 0.002 g cyanocobalamin
[2]premix contains (per 21 g) 4.0 g alpha-tocopherol acetate, 0.8 g vitamin A palmitate, 0.05 g phylloquinone, 0.006 g vitamin D3
[3]premix contains (per 133 g): 23 g choline bitartrate, 15 g 5'-CMP, 11 g 5'-GMP, 10 g 5'-UMP, 6 g 5'-AMP
[4]Carotenoids added individually as lycopene, beta carotene, and lutein (with zeaxanthin) to achieve lutein/zeaxanthin, lycopene, and beta carotene totals.
[5]Lutein/zeaxanthin mixture contains 1.25% zeaxanthin by weight of lutein.

The exemplified formulas may be prepared by making at least three separate slurries that are later blended together, heat treated, standardized, packaged and sterilized. Initially, a carbohydrate-mineral slurry is prepared by dissolving lactose in water at 65-71° C., followed by the addition of magnesium chloride, potassium citrate, potassium chloride, choline chloride, and citric acid. The resulting slurry is held with agitation at 55-65° C. for not longer than eight hours until it is later blended with the other prepared slurries.

A protein-fat slurry is prepared by combining high oleic safflower oil, soybean oil, and coconut oil at 55-60° C., followed by the addition of vitamin ADEK premix, mono- and diglycerides, lecithin, carrageenan, vitamin A, carotenoids, ARA oil, and DHA oil. Whey protein and calcium carbonate are then added. The resulting protein-oil slurry is held under moderate agitation at 40-43° C. for no longer than two hours until it is later blended with the other formed slurries.

The carbohydrate-mineral slurry is then combined with water and non-fat dry milk and agitated for 10 minutes. The protein-oil slurry is then added and the resulting mixture agitated for at least 10 minutes. Lutein and beta-carotene are then added to the blend and agitated for at least 15 minutes. The pH of the resulting blend is adjusted to 6.68-6.75 with 1 N potassium hydroxide.

After waiting for a period of not less than one minute nor greater than two hours, the resulting blend is heated to 71-82° C. and dearated under vacuum, emulsified through a single stage homogenizer at 900-1100 psig, and then heated to 99-110° C., and then heated again to 146° C. for about 5 seconds. The heated blend is passed through a flash cooler to reduce the temperature to 99-110° C. and then through a plate cooler to further reduce the temperature to 71-76° C. The cooled blend is then homogenized at 3900-4100/400-600 psig, and then held at 74-80° C. for 16 seconds, and then cooled to 1-7° C. Samples are taken for microbiological and analytical testing. The mixture is held under agitation.

A water-soluble vitamin (WSV) solution and an ascorbic acid solution are prepared separately and added to the processed blended slurry. The vitamin solution is prepared by adding the following ingredients to 9.4 kg of water with agitation: potassium citrate, ferrous sulfate, WSV premix, L-carnitine, riboflavin, and the nucleotide-choline premix. The ascorbic acid solution is prepared by adding potassium citrate and ascorbic acid to a sufficient amount of water to dissolve the ingredients. The vitamin and ascorbic acid solutions are then added to the blend, and the pH of the blend adjusted to 7-10 with 45% potassium hydroxide solution.

Based on the analytical results of the quality control tests, an appropriate amount of water is added to the batch with agitation to achieve the desired total solids. The product pH may be adjusted to achieve optimal product stability. The completed product is then placed in suitable containers and subjected to terminal sterilization.

The resulting formulas are fed to infants as a sole source of nutrition during the first 6 to 12 months of life to provide each infant with 7-300 µg/kg/day of lutein. The formulas provide improved retinal health and vision development as described herein.

Examples 2.1-2.3

The following are examples of soy-based, powder, infant formulas suitable for use in the methods of the present invention.

| INGREDIENT | Example 2.1 Amount per 454 kg | Example 2.2 Amount per 454 kg | Example 2.3 Amount per 454 kg |
|---|---|---|---|
| Water | QS | QS | QS |
| High oleic safflower oil | 52.1 kg | 52.1 kg | 52.1 kg |
| Coconut oil | 35.2 kg | 35.2 kg | 35.2 kg |
| Soy oil | 38.1 kg | 38.1 kg | 38.1 kg |
| ARA-containing oil (40% ARA) | 1.3 kg | 1.3 kg | 1.3 kg |
| DHA-containing oil (40% DHA) | 0.381 kg | 0.762 kg | 0.876 kg |
| Oil soluble vitamin premix | 0.173 kg | 0.173 kg | 0.173 kg |
| Ascorbyl palmitate | 0.162 kg | 0.162 kg | 0.162 kg |
| Soy protein isolate | 66.1 kg | 66.1 kg | 66.1 kg |
| Corn syrup | 236.0 kg | 236.0 kg | 236.0 kg |
| Calcium phosphate (di and tribasic) | 8.0 kg | 8.0 kg | 8.0 kg |
| Ferrous sulfate | 0.138 kg | 0.138 kg | 0.138 kg |
| Water soluble vitamin premix trace minerals/taurine | 0.65 kg | 0.65 kg | 0.65 kg |
| Choline chloride | 0.23 kg | 0.23 kg | 0.23 kg |
| Potassium iodide | 0.0005 kg | 0.0005 kg | 0.0005 kg |
| Methionine | 0.722 kg | 0.722 kg | 0.722 kg |
| Ascorbic acid | 0.72 kg | 0.72 kg | 0.72 kg |
| Potassium hydroxide (45% solution) | 1.2 kg | 1.2 kg | 1.2 kg |
| Potassium chloride | 0.87 kg | 0.87 kg | 0.87 kg |
| Magnesium Chloride | 0.4 kg | 0.4 kg | 0.4 kg |
| Carnitine | 0.05 kg | 0.05 kg | 0.05 kg |
| Added carotenoids[1] | —[1] | —[1] | —[1] |
| Total carotenoids (mcg/liter) | 186 | 400 | 555 |
| Total Lutein with zeaxanthin[2] (mcg/liter) | 90 | 150 | 200 |
| Total lycopene (mcg/liter) | 30 | 90 | 135 |
| Total beta carotene (mcg/liter) | 66 | 160 | 220 |

[1]Individual carotenoids added as lycopene, beta-carotene, and lutein (with zeaxanthin) to achieve lutein/zeaxanthin, lycopene, and beta-carotene totals.
[2]Lutein/zeaxanthin mixture contains 1.25% zeaxanthin by weight of lutein.

The first step in the preparation of the exemplified powder is the preparation of the oil blend. Soy oil, coconut oil and high oleic safflower oil are combined in a suitable container or tank at 60-65° C. with agitation. Ascorbyl palmitate and mixed tocopherols are added to the tank, followed by the oil soluble vitamin premix, all with agitation. Beta-carotene (BASF, Mount Olive, N.J.), and lutein (Kemin, Des Moines, Iowa) and other carotenoids are added to the oil blend and agitated until well dispersed. Soy protein isolate and methionine are then added to the oil blend, and the resulting mixture agitated and held at 54.0-60° C. until used later during the manufacturing process.

The carbohydrate-mineral slurry is then prepared. Potassium chloride, sodium chloride, magnesium chloride, and potassium iodide are added to water 60-65° C., followed by di- and tri-calcium phosphates, all with agitation. Corn syrup is then added with agitation, and the slurry held at 54-60° C. until used later during the manufacturing process.

The carbohydrate-mineral slurry is added to the oil blend. Additional water is added as necessary. The ARA and DHA oils are added to the blend. The pH of the resulting mixture is adjusted to 6.75-6.85 using KOH solution. The adjusted mixture is then held at 54-60° C. under agitation for at least 15 minutes.

The resulting mixture is then heated to 74-79° C. and deaerated under vacuum, emulsified through a single stage homogenizer at 0-2.76 Mpa, passed through a two-stage homogenizer at 6.2-7.6 MPa and 2.1-3.4 MPa. The homogenized mixture is held at 73-79° C. for 16 seconds and then cooled to 1-7° C. Samples are taken for microbiological and analytical testing. The mixture is held under agitation.

A calcium carbonate solution may be prepared for use in adjusting the calcium level of the mixture if outside of specification.

A vitamin stock solution containing a water soluble vitamin premix with trace minerals and taurine is prepared. Potassium citrate and ferrous sulfate are added to water at 37-66° C. The vitamin premix is then added and the mixture agitated. The choline chloride and carnitine are added and then the required amount of this vitamin mixture is added to the batch.

An ascorbic acid solution is prepared and added slowly to the batch with agitation for at least 10 minutes. The batch is then preheated to 74-79° C. The batch is then held for 5 seconds at 107-111° C. using direct steam injection. The batch is then cooled to 71-82° C. before being pumped to a spray dryer and dried to a flowable powder. The batch is then packaged in suitable containers and sealed under a headspace of less than 2.0% oxygen.

The exemplified powders are reconstituted with water to a caloric density of 676 kcal/liter. The resulting liquid formulas are fed to preterm infants as a sole source of nutrition at 7-300 µg/kg/day of lutein. The formula provides improved retinal health and vision development as described herein, and reduces the risk or severity of retinopathy of prematurity in the infants.

Examples 3.1-3.3

The following are examples of milk-based, powder, infant formulas suitable for use in the methods described herein.

| Ingredient Name | Example 3.1 Amount per 454 kg | Example 3.2 Amount per 454 kg | Example 3.3 Amount per 454 kg |
|---|---|---|---|
| Water | QS | QS | QS |
| Soy oil | 35.8 kg | 35.8 kg | 35.8 kg |
| Coconut oil | 23.8 kg | 23.8 kg | 23.8 kg |
| MCT oil (medium chain triglyceride) | 32.1 kg | 32.1 kg | 32.1 kg |
| High Oleic Safflower oil | 34.6 kg | 34.6 kg | 34.6 kg |
| Ascorbyl palmitate | 0.157 kg | 0.157 kg | 0.157 kg |
| Vitamin A palmitate | 0.002 kg | 0.002 kg | 0.002 kg |
| Vitamin ADEK premix[1] | 0.192 kg | 0.192 kg | 0.192 kg |
| Mixed tocopherols | 0.075 kg | 0.075 kg | 0.075 kg |
| Whey protein concentrate | 32.7 kg | 32.7 kg | 32.7 kg |
| Calcium carbonate | 1.2 kg | 1.2 kg | 1.2 kg |
| Lactose | 54.5 kg | 54.5 kg | 54.5 kg |
| Corn syrup solids | 117.1 kg | 117.1 kg | 117.1 kg |
| Magnesium chloride | 0.724 kg | 0.724 kg | 0.724 kg |
| Potassium citrate | 2.8 kg | 2.8 kg | 2.8 kg |
| Sodium chloride | 0.39 kg | 0.39 kg | 0.39 kg |
| Sodium citrate | 0.001 kg | 0.001 kg | 0.001 kg |
| Non-fat dried milk | 116.9 kg | 116.9 kg | 116.9 kg |
| Calcium phosphate tribasic | 1.8 kg | 1.8 kg | 1.8 kg |
| ARA-containing oil (40% ARA) | 1.3 kg | 1.3 kg | 1.3 kg |
| DHA-containing oil (40% DHA) | 0.43 kg | 0.65 kg | 1.00 kg |
| Ascorbic acid | 1.29 kg | 1.29 kg | 1.29 kg |
| Potassium hydroxide 1N solution | 9.8 kg | 9.8 kg | 9.8 kg |
| Ferrous sulfate | 0.168 kg | 0.168 kg | 0.168 kg |
| Carnitine | 0.136 kg | 0.136 kg | 0.136 kg |
| Choline chloride | 0.182 kg | 0.182 kg | 0.182 kg |
| Vit. and trace mineral premix[2] | 0.825 kg | 0.825 kg | 0.825 kg |
| Inositol | 0.734 kg | 0.734 kg | 0.734 kg |
| Nucleotide, choline bitartrate premix[3] | 1.1 kg | 1.1 kg | 1.1 kg |
| Added carotenoids[4] | —[4] | —[4] | —[4] |
| Total carotenoids (mcg/liter) | 186 | 400 | 555 |
| Total Lutein with zeaxanthin[5] (mcg/liter) | 90 | 150 | 200 |
| Total lycopene (mcg/liter) | 30 | 90 | 135 |
| Total beta carotene (mcg/liter) | 66 | 160 | 220 |

[1]Premix provides 71 gm d-alpha-tocopheryl acetate, 7.29 gm Vitamin A palmitate, 0.422 gm phylloquinone, and 0.051 gm Vitamin D3 to the product.
[2]Premix provides 252 gm taurine, 183 gm inositol, 84.5 gm zinc sulfate, 53.8 gm niacinamide, 32.6 gm calcium pantothenate, 29 gm ferrous sulfate, 10.1 gm cupric sulfate, 8.4 gm thiamine, 3.7 gm riboflavin, 3.4 gm pyridoxine (HCl), 1.1 gm folic acid, 1.0 gm manganese sulfate, 0.3 gm biotin, 0.2 gm sodium selenate, and 0.03 gm cyanocobalamin to the product.
[3]Premix provides 188 gm choline bitartrate, 118 gm cytidine 5'-monophosphate, 92 gm disodium guanosine 5'-monophosphate, 80 gm disodium uridine 5'-monophosphate, and 51 gm adenosine 5'-monophosphate to the product.
[4]Individual carotenoids added as lycopene, beta-carotene, and lutein (with zeaxanthin) to achieve lutein/zeaxanthin, lycopene, and beta-carotene totals.
[5]Lutein/zeaxanthin mixture contains 1.25% zeaxanthin by weight of lutein.

This powder formula is manufactured by preparing at least two slurries that are later blended together, heat treated, standardized, spray dried and packaged. Initially, a carbohydrate-mineral slurry is prepared (45-50% solids) by dissolving lactose in water at 66-76° C. Corn syrup solids are then added and allowed to dissolve, followed by the addition of magnesium chloride, potassium citrate, sodium chloride, choline chloride, and sodium citrate, all with agitation. The resulting carbohydrate-mineral slurry is held at 54-60° C. under agitation until used later during the manufacturing process.

A protein-fat slurry is prepared by combining high oleic safflower oil, coconut oil, soy oil, and MCT oil at 40.5-49° C., followed by ascorbyl palmitate, mixed tocopherols, vitamin A palmitate, and the vitamin ADEK premix, all with agitation. Lutein (Kemin, Des Moines, Iowa) and other carotenoids, are then added with agitation. Whey protein concentrate is then added to the slurry, followed by calcium carbonate and calcium phosphate tribasic, all with agitation. The completed protein-fat slurry is held under moderate agitation at 54-60° C. for no longer than twelve hours until it is blended with the other prepared slurries.

The carbohydrate-mineral slurry is transferred to a tank in which a sufficient amount of water is added to create a final blend slurry of approximately 50% solids. Non-fat dry milk is then added to the blend and allowed to solubilize. The protein-fat slurry is then added and the entire blend slurry is allowed to agitate for at least 15 minutes. The resulting blend is maintained at 60-65° C. The blend pH is adjusted to 6.7-6.9 with 1 N KOH.

After waiting for a period of not less than one minute nor greater than two hours, the resulting blend is heated to 71-79° C., emulsified at 2.75-4.1 Mpa, and then heated to 115-127° C. for about 5 seconds using direct steam injection. The heated emulsion is then flash cooled to 87-99° C., and homogenized at 9.7-11.0/2.75-4.1 MPa. The homogenized slurry is then cooled to 1.6-7.2° C. Samples are taken for microbiological and analytical testing. The mixture is held under agitation.

A vitamin-trace mineral solution is prepared by adding the following ingredients to the required amount of water, under agitation: potassium citrate, ferrous sulfate, carnitine, vitamin and the trace mineral premix, inositol, and nucleotide and choline bitartrate premix. The vitamin-trace mineral solution is then added to the homogenized slurry under agitation.

An ascorbic acid solution is prepared by adding potassium citrate and ascorbic acid to water with agitation, and then adding the aqueous mixture to the homogenized slurry under agitation.

The product is preheated to 65.5-77° C. The product is then held at 82-90.5° C. for 5 seconds before being flash cooled to 71-82° C. and pumped to the spray dryer. The product is spray dried to produce a desired free-flowing powder. The resulting powder is packaged under nitrogen to maximize product stability and flavor.

The exemplified powders are reconstituted with water to a caloric density of 676 kcal/liter. The resulting liquid formulas are fed to preterm infants as a sole source of nutrition during the first 6 to 12 months of life to provide 7-300 µg/kg/day of lutein. The formula provides improved retinal health and vision development as described herein, and reduces the risk or severity of retinopathy of prematurity in the infants.

Examples 4.1-4.3

The following are examples of concentrated human milk fortifier liquids for use in the methods described herein.

| Ingredient Name | Example 4.1 Gm per kg | Example 4.2 Gm per kg | Example 4.3 Gm per kg |
|---|---|---|---|
| Sucrose | 125.5 | 125.5 | 125.5 |
| Milk protein isolate | 64.6 | 64.6 | 64.6 |
| Coconut oil | 30.2 | 30.2 | 30.2 |
| Whey protein concentrate | 24.4 | 24.4 | 24.4 |
| MCT Oil | 21.9 | 21.9 | 21.9 |
| Soy Oil | 21.9 | 21.9 | 21.9 |
| Tricalcium phosphate | 14.4 | 14.4 | 14.4 |
| Potassium chloride | 5.18 | 5.18 | 5.18 |
| Calcium carbonate | 3.44 | 3.44 | 3.44 |
| Magnesium phosphate | 3.05 | 3.05 | 3.05 |
| Potassium citrate | 1.32 | 1.32 | 1.32 |
| DHA (docosahexaenoic acid) oil | 0.2 | 0.2 | 0.2 |
| Soy lecithin | 0.756 | 0.756 | 0.756 |
| ARA (arachidonic acid) oil | 0.729 | 0.729 | 0.729 |
| Dipotassium phosphate | 0.596 | 0.596 | 0.596 |
| Monopotassium phosphate | 0.466 | 0.466 | 0.466 |
| Vitamin E | 0.357 | 0.357 | 0.357 |
| Sodium chloride | 0.170 | 0.170 | 0.170 |
| KOH 5% solution | Q.S. | Q.S. | Q.S. |
| m-Inositol | 0.0698 | 0.0698 | 0.0698 |
| Ascorbic acid | 0.913 | 0.913 | 0.913 |
| Taurine | 0.0663 | 0.0663 | 0.0663 |
| Niacinamide | 0.0582 | 0.0582 | 0.0582 |
| Vitamin A | 0.0494 | 0.0494 | 0.0494 |
| Zinc sulfate | 0.0461 | 0.0461 | 0.0461 |
| Calcium pantothenate | 0.0286 | 0.0286 | 0.0286 |
| Ferrous sulfate | 0.0136 | 0.0136 | 0.0136 |
| Cupric sulfate | 0.00836 | 0.00836 | 0.00836 |
| Riboflavin | 0.00763 | 0.00763 | 0.00763 |
| Thiamine chloride HCL | 0.00507 | 0.00507 | 0.00507 |
| Pyridoxine HCL | 0.00459 | 0.00459 | 0.00459 |
| Folic acid | 0.000778 | 0.000778 | 0.000778 |
| Manganese Sulfate | 0.000573 | 0.000573 | 0.000573 |
| Biotin | 0.000507 | 0.000507 | 0.000507 |
| Vitamin K | 0.000835 | 0.000835 | 0.000835 |
| Vitamin D3 | 0.000235 | 0.000235 | 0.000235 |
| Sodium selenate | 0.0000491 | 0.0000491 | 0.0000491 |
| Potassium iodide | 0.0000105 | 0.0000105 | 0.0000105 |
| Cyanocobalamin | 0.0000103 | 0.0000103 | 0.0000103 |
| Added carotenoids[1] | —[1] | —[1] | —[1] |
| Total carotenoids (mcg/liter) | 186 | 400 | 555 |
| Total Lutein with zeaxanthin[2] (mcg/liter) | 90 | 150 | 200 |
| Total lycopene (mcg/liter) | 30 | 90 | 135 |
| Total beta carotene (mcg/liter) | 66 | 160 | 220 |

[1]Individual carotenoids added as lycopene, beta-carotene, and lutein (with zeaxanthin) to achieve the lutein/zeaxanthin, lycopene, and beta-carotene totals.
[2]Lutein/zeaxanthin mixture contains 1.25% zeaxanthin by weight of lutein.

The ingredients listed in the preceding table are combined and processed to form a concentrated human milk fortifier embodiment of the present invention. One method of preparing such an embodiment is described below.

An initial intermediate blend is prepared by heating to 32-37° C. the specified amounts of coconut oil, MCT oil, soy oil, DHA oil and AA oil, all with agitation. A soy lecithin emulsifier is added with agitation to the heated blend and allowed to dissolve. Vitamins A, D, and K, Natural Vitamin E, and lutein are then added with agitation to the developing blend. Milk protein isolate (25.8 kg) and the specified amounts of ultra micronized tricalcium phosphate and calcium carbonate are added to the blend. The resulting intermediate blend is maintained at 26-48° C. under moderate agitation for a period of time not to exceed six hours before being added to the aqueous protein blend described below.

An aqueous protein blend is then prepared by heating 573 kg of ingredient water at 48-60° C., and then adding to it with agitation milk protein isolate (38.8 kg) and the specified amount of whey protein concentrate. Thereafter, and with agitation, the entire intermediate blend described above is added to the aqueous protein blend. The following ingredients are then added to the resulting blend in the following order: potassium citrate, dipotassium phosphate, monopotassium phosphate, magnesium phosphate, sodium chloride, potassium chloride, potassium iodide and sucrose. After no less than five minutes, the blend pH is adjusted to 6.60-6.80 using a 1 N KOH solution, and thereafter maintained at 51-60° C., for a period of time not to exceed two hours before further processing.

The pH adjusted blend is then homogenized using one or more in-line homogenizers at pressures from 1000-4000 psig with or without a second stage homogenization from 100-500 psig followed by heat treatment using a HTST (high temperature short time, 74° C. for 16 seconds) or UHTST (ultra-high temperature short time, 132-154° C. for 5-15 seconds) process. The choice of UHTST or HTST is normally made based upon a review of the bioburden of each of the ingredients in the formulation. After the appropriate heat treatment, the batch is cooled in a plate cooler to 1.0-5.0° C. and then transferred to a refrigerated holding tank, where it is subjected to analytical testing and then standardized to finished product specifications, which includes the addition of an ascorbic acid solution and a water-soluble vitamin and trace mineral solution, all of which is prepared separately before adding to the previously described refrigerated batch.

The ascorbic acid solution is prepared by adding the specified amount of ascorbic acid to 11.1 kg of 1 N KOH solution with agitation. The water-soluble vitamin and trace mineral solution is prepared by heating 25.2 kg of ingredient water to 37° C. to 48° C. The water soluble vitamins and trace minerals are added to the water as a premix which contains m-inositol, taurine, niacinamide, zinc sulfate, calcium pantothenate, ferrous sulfate, cupric sulfate, riboflavin, thiamine hydrochloride, pyridoxine hydrochloride, folic acid, manganese sulfate, biotin, sodium selenate, and cyanocobalamin. As noted above, both solutions are then added to the refrigerated batch, all with agitation. As part of batch standardization, the appropriate amount of ingredient dilution water is then added to the batch for a target total solids level of 31%, and the pH adjusted to 7.1 with a 1 N KOH solution. The batch is filled into suitably sized containers containing 5 ml of product.

The exemplified human milk fortifier concentrates are combined with human milk (5 ml concentrate with 20-25 ml human milk). The fortified human milk is then fed to pre-term infants to provide 7-300 µg/kg/day of lutein. The formula provides improved retinal health and vision development as described herein, including reduced risk of retinopathy of prematurity.

Examples 5.1-5.3

This example illustrates a ready-to-feed, preterm infant formula embodiment of the present invention. This formula is similar to Similac® Special Care® Advance® with Iron Premature Infant formula, a preterm infant formula available from Abbott Laboratories, Columbus, Ohio, except for the increased lutein concentrations and subsequent lutein to docosahexaenoic acid ratios.

The preterm infant formula includes nonfat milk, corn syrup solids, lactose, medium chain triglycerides, whey protein concentrate, soy oil, coconut oil, *C. cohnii* oil (source of docosahexaenoic acid), *M. alpina* oil (source of arachidonic acid), calcium phosphate, calcium carbonate, potassium citrate, ascorbic acid, magnesium chloride, soy lecithin, mono- and diglycerides, m-inositol, sodium citrate, carrageenan, ferrous sulfate, choline bitartrate, taurine, choline chloride, niacinamide, d-alpha-tocopheryl acetate, L-carnitine, zinc sulfate, potassium chloride, potassium phosphate dibasic, calcium pantothenate, cupric sulfate, vitamin A palmitate, riboflavin, thiamine chloride hydrochloride, pyridoxine hydrochloride, folic acid, beta-carotene, manganese sulfate, biotin, phylloquinone, sodium selenate, vitamin D3, cyanocobalamin and nucleotides (cytidine 5'-monophosphate, disodium guanosine 5'-monophosphate, disodium uridine 5'-monophosphate, adenosine 5'-monophosphate). A carotenoid supplement is added to the formula.

The above-referenced ingredients are formulated together by conventional methods to provide the following nutrition profile:

| Nutrients | Example 5.1 Amount per 100 kcal (or 123 ml) | Example 5.2 Amount per 100 kcal (or 123 ml) | Example 5.3 Amount per 100 kcal (or 123 ml) |
| --- | --- | --- | --- |
| Protein (from nonfat milk, whey protein concentrate) | 3.00 g | 3.00 g | 3.00 g |
| Fat (form 50:30:18.3 mix of MCT oil, soy oil, and coconut oils; ____ mg DHA, ____ mg ARA; 700 mg linoleic acid) | 5.43 g | 5.43 g | 5.43 g |
| Carbohydrate (source - 50:50 mix of corn syrup solids, lactose) | 10.3 g | 10.3 g | 10.3 g |
| Lutein | 18.4 mcg | 37 mcg | 9141 mcg |
| Vitamin A | 1250 IU | 1250 IU | 1250 IU |
| Vitamin D | 150 IU | 150 IU | 150 IU |
| Vitamin E | 4.0 IU | 4.0 IU | 4.0 IU |
| Vitamin K | 12 mcg | 12 mcg | 12 mcg |
| Thiamine | 250 mcg | 250 mcg | 250 mcg |
| Riboflavin | 620 mcg | 620 mcg | 620 mcg |
| Vitamin B6 | 250 mcg | 250 mcg | 250 mcg |
| Vitamin B12 | 0.55 mcg | 0.55 mcg | 0.55 mcg |
| Niacin | 5000 mcg | 5000 mcg | 5000 mcg |
| Folic acid | 37 mcg | 37 mcg | 37 mcg |
| Pantothenic acid | 1900 mcg | 1900 mcg | 1900 mcg |
| Biotin | 37.0 mcg | 37.0 mcg | 37.0 mcg |
| Ascorbic acid | 37 mg | 37 mg | 37 mg |
| Choline | 10 mg | 10 mg | 10 mg |
| Inositol | 40.0 mg | 40.0 mg | 40.0 mg |
| Calcium | 180 mg (9.0 mEq) | 180 mg (9.0 mEq) | 180 mg (9.0 mEq) |
| Phosphorus | 100 mg | 100 mg | 100 mg |
| Magnesium | 12.0 mg | 12.0 mg | 12.0 mg |
| Iron | 1.8 mg | 1.8 mg | 1.8 mg |
| Zinc | 1.50 mcg | 1.50 mcg | 1.50 mcg |
| Manganese | 12 mcg | 12 mcg | 12 mcg |
| Copper | 250 mcg | 250 mcg | 250 mcg |
| Iodine | 6 mcg | 6 mcg | 6 mcg |
| Selenium | 1.8 mcg | 1.8 mcg | 1.8 mcg |
| Sodium | 43 mg (1.9 mEq) | 43 mg (1.9 mEq) | 43 mg (1.9 mEq) |
| Potassium | 129 mg (3.3 mEq) | 129 mg (3.3 mEq) | 129 mg (3.3 mEq) |
| Chloride | 81 mg (2.3 mEq) | 81 mg (2.3 mEq) | 81 mg (2.3 mEq) |
| Added carotenoids[1] | —[1] | —[1] | —[1] |
| Total carotenoids (mcg/liter) | 186 | 400 | 555 |
| Total Lutein w/ zeaxanthin[2] (mcg/liter) | 90 | 150 | 200 |
| Total lycopene (mcg/liter) | 30 | 90 | 135 |
| Total beta carotene (mcg/liter) | 66 | 160 | 220 |

[1] Individual carotenoids added as lycopene, beta-carotene, and lutein (with zeaxanthin) to achieve the lutein/zeaxanthin, lycopene, and beta-carotene totals.
[2] Lutein/zeaxanthin mixture contains 1.25% zeaxanthin by weight of lutein.

Example 5.4

Skin carotenoid levels are measured in a preterm infant born at 26 weeks gestation, weighing 1.7 kg, age 1 day. Skin carotenoid levels are measured (800 Raman Counts) using non invasive Raman Spectroscopy on the infant's palm. The infant is administered the preterm infant formula of Example 5.2 as a primary form of daily nutrition until discharge. The formula contains lutein, lycopene, beta carotene, and zeaxanthin. Skin carotenoids are measured periodically until discharge to assure adequate carotenoid supplementation as noted by increasing skin carotenoid levels (increased Raman Counts). The infant subsequently experiences minimal or no signs of retinopathy of prematurity.

The exemplified ready-to-feed formulas (caloric density of 812 kcal/liter) are administered to preterm infants to provide from 7-300 mcg/kg of lutein per day. The administered formula improves eye health as described herein, and are especially useful as applied to preterm infants to reduce the risk of retinopathy of prematurity and helps protect the eyes from natural or artificial light, especially biliary lights.

Experiment

A study is conducted to compare plasma lutein concentrations in breastfed infants with plasma lutein concentrations in formula fed infants. The latter received one of three formulas defined by lutein concentrations of 32.6 mcg/liter (L1), 52.6 mcg/liter (L2), or 14.6 mcg/liter (CTRL). The study groups and resulting plasma lutein concentrations are summarized in the following table.

| Feeding Group | Plasma Lutein (mcg/dL) ‡ | |
|---|---|---|
| | Study Day 1 | Study Day 56 |
| Control (CTRL) - no added lutein Total inherent lutein 14.6 mcg/liter lutein) | 1.37 ± 0.29 $^a$ (0.40-5.10) 20 | 2.17 ± 0.12 $^a$ (1.16-3.25) 18 |
| Formula L1 Added lutein approximately 18 mcg/liter Inherent lutein approximately 14.6 mcg/liter Total lutein 32.6 mcg/L | 0.78 ± 0.09 $^a$ (0.27-2.09) 24 | 2.21 ± 0.16 $^a$ (0.20-3.61) 22 |
| Formula L2 Added lutein approximately 38 mcg/liter Inherent lutein approximately 14.6 mcg/liter Total lutein 52.6 mcg/L | 0.97 ± 0.13 $^a$ (0.20-2.31) 21 | 3.25 ± 0.26 $^b$ (0.60-4.70) 19 |
| Human Milk (HM) 6.5-107.8 mcg/liter lutein | 6.53 ± 0.54 $^b$ (1.69-14.12) 24 | 5.88 ± 0.77 $^c$ (0.49-20.09) 26 |

‡ Values are presented as mean ± SEM, (range) n Values in a column with superscripts without a common letter differ($p < 0.05$). See text for actual p values. Statistical comparisons among the formula groups are done using the Kruskal-Wallis test. Comparisons between the formula groups and the human milk group are done using the Wilcoxon rank-sum test.

Plasma lutein concentrations (at day 56 of the study) are used as the primary variable in the study. The primary comparison is the difference in plasma lutein concentrations between the L2 and CTRL formula groups. Secondary comparisons included differences in plasma lutein concentrations among the formula groups (CTRL, L1, L2) and differences between the formula groups and the human milk group. Plasma lutein concentrations on day 56 from a total of 85 infants (CTRL, n=18; L1, n=22; L2, n=19; HM, n=26) is used in these analyses and results reported as mean±SEM in the following table.

Infants in the L2 formula group have significantly higher ($p<0.05$) plasma concentrations of lutein than infants in the L1 and CTRL formula groups. Plasma lutein are not different between the L1 and CTRL formula groups. The human milk group has higher plasma lutein concentrations than the CTRL ($p<0.0001$), L1 ($p<0.0001$), and L2 ($p=0.0052$) formula groups. Plasma lutein concentration is significantly correlated with lutein intake ($r=0.436$, $p=0.0014$). Lutein intake and plasma response from the study are also summarized in FIG. 1.

The data from the study show that lutein is surprisingly less bioavailable from infant formula than from human milk (see FIG. 1). As such, in order for an infant formula to produce plasma lutein concentrations in infants similar to that produced by feeding human milk, an infant formula must be formulated to contain at least about 50 mcg/liter of lutein, preferably from 100 mcg/liter to about 200 mcg/liter.

Study: Skin Carotenoids

A purpose of this study is to evaluate the relation of skin carotenoids in the development or severity of Retinopathy of Prematurity (ROP) in human milk fed preterm infants. Skin carotenoid levels are measured using non-invasive Raman spectroscopy. It is known that skin carotenoid levels as measured by Raman spectroscopy correlate with serum and tissue carotenoid levels (Hata et al., *J Invest Dermatology* 115; 441, 2000; Ermakov et al., *Optics Letters*, 26:1179, 2001).

Skin carotenoids are assessed non-invasively using a BioPhotonic Scanner (available from Pharmanex, Provo, Utah USA). For each infant tested, a small area of the palm is exposed to a low-energy monochromatic laser light of 473 nm (blue light) penetrating into the stratum corneum layer of the skin for approximately 3 minutes to obtain an adequate measurement. Carotenoids present in the exposed area will shift the wavelength to 511 nm (green light), which is detected into a relative signal and converted to Raman Counts (RC).

Carotenoid molecules are strong Raman scatterers when excited with wavelengths of light between 450 and 500 nanometers (nm). This range of visible light can be accomplished with commercially available laser light sources. The carotenoid molecules are especially suited for this analysis since their characteristic double diene bonds emit strong and measurable Raman spectroscopic signals (511 nm) when excited with laser light of 473 nm.

In the present study, twenty-two infants whose individual birth weights (BW) are less than 1800 g, gestation at less than 33 weeks, and fed their own mother's milk are enrolled at the start of feedings. Skin carotenoids are measured initially and then biweekly. Days on oxygen are recorded. Initial eye exams for ROP are initiated between 4 and 7 weeks of age. The mean gestation (±SD) is 28±2.6 weeks with mean BW of 1102±356 g. Forty-one percent of the infants (9/22) develop ROP, with 3 requiring laser surgery for stage 3 ROP. Infants with ROP have lower mean gestation (26 v 30 wks), BW (871 v 1262 g) and longer on oxygen (112 v 40 days) than infants with no ROP.

After controlling for prematurity, it is also discovered that infants who develop ROP have lower initial skin carotenoid levels than infants who had no ROP, 7.8±7.8 v 11.1±4.2 (Mann Whitney, $P<0.02$). ROP is negatively associated with initial skin carotenoids ($R=-0.75$, $P<0.001$). Skin carotenoids are positively associated with birth weight ($R=0.66$, $P<0.001$), gestation ($R=0.69$, $P<0.001$), day of life ($R=0.64$, $P<0.001$), but negatively associated with days on oxygen ($R=-0.57$, $P<0.01$).

This study shows that ROP is influenced by skin carotenoid (lutein, beta-carotene, zeaxanthin, lycopene) levels found in preterm infants fed human milk. The study suggests that preterm infants at risk of developing ROP can be monitored for skin carotenoid concentrations and may benefit from carotenoid supplementation. This may result in reducing the risk or severity of ROP.

What is claimed is:

1. A liquid human milk fortifier comprising:
    protein, carbohydrate, fat, docosahexaenoic acid, and at least about 200 mcg of lutein per liter of liquid human milk fortifier, wherein the lutein is a synthetic lutein; wherein a weight ratio of lutein (mcg) to docosahexaenoic acid (mg) is from about 1:2 to about 10:1; and wherein the liquid human milk fortifier is free of egg phospholipids.

2. The liquid human milk fortifier of claim 1, wherein the liquid human milk fortifier has a total solids level of about 31%.

3. The liquid human milk fortifier of claim 1, wherein liquid human milk fortifier comprises from about 200 mcg to about 1,150 mcg of lutein per liter of liquid human milk fortifier.

4. The liquid human milk fortifier of claim 3, wherein the weight ratio of lutein (mcg) to docosahexaenoic acid (mg) is from about 1:2 to about 9:1.

5. The liquid human milk fortifier of claim 3, wherein the weight ratio of lutein (mcg) to docosahexaenoic acid (mg) is from about 1:2 to about 5:1.

6. The liquid human milk fortifier of claim 3, wherein the liquid human milk fortifier further comprises beta-carotene, lycopene, and zeaxanthin, and wherein the liquid human milk fortifier has a total carotenoid concentration of up to about 2,000 mcg of total carotenoid per liter of liquid human milk fortifier.

7. The liquid human milk fortifier of claim 3, wherein the protein comprises hydrolyzed casein.

8. The liquid human milk fortifier of claim 1, packaged into a container containing about 5 mL of the liquid human milk fortifier.

9. A synthetic liquid human milk fortifier comprising:
protein, carbohydrate, fat, docosahexaenoic acid, and at least about 200 mcg of lutein per liter of synthetic liquid human milk fortifier;
wherein a weight ratio of lutein (mcg) to docosahexaenoic acid (mg) is from about 1:2 to about 10:1; and
wherein the liquid human milk fortifier is free of egg phospholipids.

10. The synthetic liquid human milk fortifier of claim 9, wherein the synthetic liquid human milk fortifier has a total solids level of about 31%.

11. The synthetic liquid human milk fortifier of claim 9, wherein the synthetic liquid human milk fortifier comprises from about 200 mcg/liter to about 1,150 mcg of lutein per liter of synthetic liquid human milk fortifier.

12. The synthetic liquid human milk fortifier of claim 11, wherein the weight ratio of lutein (mcg) to docosahexaenoic acid (mg) is from about 1:2 to about 9:1.

13. The synthetic liquid human milk fortifier of claim 11, wherein the weight ratio of lutein (mcg) to docosahexaenoic acid (mg) is from about 1:2 to about 5:1.

14. The synthetic liquid human milk fortifier of claim 11, wherein the synthetic liquid human milk fortifier further comprises beta-carotene, lycopene, and zeaxanthin, and wherein the synthetic liquid human milk fortifier has a total carotenoid concentration of up to about 2,000 mcg of total carotenoid per liter of liquid human milk fortifier.

15. The synthetic liquid human milk fortifier of claim 11, wherein the protein comprises hydrolyzed casein.

16. The synthetic liquid human milk fortifier of claim 9, packaged into a container containing about 5 mL of the synthetic liquid human milk fortifier.

* * * * *